United States Patent
Long et al.

(10) Patent No.: US 11,382,796 B2
(45) Date of Patent: *Jul. 12, 2022

(54) REDUCED-PRESSURE SURGICAL WOUND TREATMENT SYSTEMS AND METHODS

(71) Applicant: KCI Licensing, Inc., San Antonio, TX (US)

(72) Inventors: Justin Alexander Long, Lago Vista, TX (US); Richard Marvin Kazala, Jr., San Antonio, TX (US); Robert Peyton Wilkes, San Antonio, TX (US); Eric Woodson Barta, Castle Hills, TX (US); Matthew Francis Cavanaugh, II, San Antonio, TX (US); Larry Tab Randolph, San Antonio, TX (US); Li Yao, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 177 days.

This patent is subject to a terminal disclaimer.

(21) Appl. No.: 16/740,004

(22) Filed: Jan. 10, 2020

(65) Prior Publication Data

US 2020/0146894 A1 May 14, 2020

Related U.S. Application Data

(63) Continuation of application No. 15/411,395, filed on Jan. 20, 2017, now Pat. No. 10,568,768, which is a
(Continued)

(51) Int. Cl.
*A61F 13/00* (2006.01)
*A61M 1/00* (2006.01)
(Continued)

(52) U.S. Cl.
CPC .. *A61F 13/00059* (2013.01); *A61F 13/00017* (2013.01); *A61F 13/00029* (2013.01);
(Continued)

(58) Field of Classification Search
CPC .......... A61F 13/00004; A61F 13/00008; A61F 13/00017; A61F 13/00029;
(Continued)

(56) References Cited

U.S. PATENT DOCUMENTS

| 1,195,430 A | 8/1916 | Angier |
| 1,355,846 A | 10/1920 | Rannells |

(Continued)

FOREIGN PATENT DOCUMENTS

| AU | 550575 B2 | 3/1986 |
| AU | 745271 B2 | 3/2002 |

(Continued)

OTHER PUBLICATIONS

Laskin, et al.; "Minimally Invasive Total Knee Replacement Through a Mini-Midvastus Incision: An Outcome Study," Surgical Technology International XIII, 2004; 231-8.
(Continued)

*Primary Examiner* — Keri J Nelson

(57) ABSTRACT

A reduced-pressure system for treating tissue, such as damaged subcutaneous tissue, includes a shaped dressing bolster for placing on the patient's epidermis and substantially sized to overlay the damaged subcutaneous tissue. The system further includes a sealing subsystem for providing a fluid seal over the shaped dressing bolster and a portion of the patient's epidermis, and a reduced-pressure subsystem for delivering a reduced pressure to the sealing subsystem. The reduced-pressure system may develop a force, which may include a vertical force that is realized at tissue site deeper than the epidermis or a closing force directed towards the
(Continued)

incision. The shaped dressing bolster is shaped to evenly distribute the force. Other methods and systems are included.

20 Claims, 13 Drawing Sheets

Related U.S. Application Data continuation of application No. 12/475,398, filed on May 29, 2009, now Pat. No. 9,572,719.

(60) Provisional application No. 61/144,067, filed on Jan. 12, 2009, provisional application No. 61/121,362, filed on Dec. 10, 2008, provisional application No. 61/057,797, filed on May 30, 2008, provisional application No. 61/057,798, filed on May 30, 2008, provisional application No. 61/057,800, filed on May 30, 2008, provisional application No. 61/057,802, filed on May 30, 2008, provisional application No. 61/057,803, filed on May 30, 2008, provisional application No. 61/057,805, filed on May 30, 2008, provisional application No. 61/057,807, filed on May 30, 2008, provisional application No. 61/057,808, filed on May 30, 2008, provisional application No. 61/057,810, filed on May 30, 2008.

(51) Int. Cl.
  *A61F 13/02* (2006.01)
  *A61L 15/60* (2006.01)
  *A61H 1/00* (2006.01)
  *A61F 15/00* (2006.01)

(52) U.S. Cl.
  CPC .. *A61F 13/00034* (2013.01); *A61F 13/00038* (2013.01); *A61F 13/00068* (2013.01); *A61F 13/022* (2013.01); *A61F 13/0209* (2013.01); *A61F 13/0216* (2013.01); *A61F 13/0223* (2013.01); *A61F 13/0243* (2013.01); *A61F 13/0289* (2013.01); *A61F 15/008* (2013.01); *A61H 1/008* (2013.01); *A61L 15/60* (2013.01); *A61M 1/0023* (2013.01); *A61M 1/71* (2021.05); *A61M 1/90* (2021.05); *H05K 999/99* (2013.01); *A61F 13/00* (2013.01); *A61F 2013/0028* (2013.01); *A61F 2013/0054* (2013.01); *A61F 2013/00131* (2013.01); *A61F 2013/00136* (2013.01); *A61F 2013/00174* (2013.01); *A61F 2013/00182* (2013.01); *A61F 2013/00246* (2013.01); *A61F 2013/00536* (2013.01); *A61F 2013/00748* (2013.01); *A61M 2205/70* (2013.01); *A61M 2207/00* (2013.01); *A61M 2210/1007* (2013.01); *A61M 2210/1021* (2013.01); *Y10T 29/49* (2015.01); *Y10T 29/49826* (2015.01)

(58) Field of Classification Search
  CPC .......... A61F 13/00034; A61F 13/00038; A61F 13/00059; A61F 13/00068; A61F 13/0209; A61F 13/0216; A61F 13/022; A61F 13/0223; A61F 13/0243; A61F 13/0289; A61F 2013/0028; A61M 1/71; A61M 1/90; A61L 15/60
  See application file for complete search history.

(56) References Cited

U.S. PATENT DOCUMENTS

| | | |
|---|---|---|
| 1,638,043 A | 8/1927 | Lee |
| 1,845,630 A | 2/1932 | Scholl |
| 2,452,345 A | 10/1948 | Anseimo |
| 2,547,758 A | 4/1951 | Keeling |
| 2,632,443 A | 3/1953 | Lesher |
| 2,682,873 A | 7/1954 | Evans et al. |
| 2,896,618 A | 7/1959 | Schaefer |
| 2,910,763 A | 11/1959 | Lauterbach |
| 2,969,057 A | 1/1961 | Simmons |
| 3,026,874 A | 3/1962 | Stevens |
| 3,066,672 A | 12/1962 | Crosby, Jr. et al. |
| 3,367,332 A | 2/1968 | Groves |
| 3,419,006 A | 12/1968 | Warwick |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 3,892,229 A | 7/1975 | Taylor et al. |
| 3,903,882 A | 9/1975 | Augurt |
| 3,969,561 A | 7/1976 | Marshall |
| 4,080,970 A | 3/1978 | Miller |
| 4,091,804 A | 5/1978 | Hasty |
| 4,096,853 A | 6/1978 | Weigand |
| 4,121,582 A | 10/1978 | Masso Remiro |
| 4,139,004 A | 2/1979 | Gonzalez, Jr. |
| 4,165,748 A | 8/1979 | Johnson |
| 4,184,510 A | 1/1980 | Murry et al. |
| 4,224,945 A | 9/1980 | Cohen |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,266,545 A | 5/1981 | Moss |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,375,217 A | 3/1983 | Arkans |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,430,998 A | 2/1984 | Harvey et al. |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,572,814 A | 2/1986 | Naylor et al. |
| 4,605,399 A | 8/1986 | Weston et al. |
| 4,608,041 A | 8/1986 | Nielsen |
| 4,612,230 A | 9/1986 | Liland et al. |
| 4,640,688 A | 2/1987 | Hauser |
| 4,655,754 A | 4/1987 | Richmond et al. |
| 4,663,352 A | 5/1987 | Onofrj |
| 4,664,662 A | 5/1987 | Webster |
| 4,710,165 A | 12/1987 | McNeil et al. |
| 4,722,332 A | 2/1988 | Saggers |
| 4,727,868 A | 3/1988 | Szycher et al. |
| 4,733,659 A | 3/1988 | Edenbaum et al. |
| 4,743,232 A | 5/1988 | Kruger |
| 4,751,133 A | 6/1988 | Szycher et al. |
| 4,758,220 A | 7/1988 | Sundblom et al. |
| 4,770,490 A | 9/1988 | Gruenewald et al. |
| 4,787,888 A | 11/1988 | Fox |
| 4,795,435 A | 1/1989 | Steer |
| 4,826,494 A | 5/1989 | Richmond et al. |
| 4,838,883 A | 6/1989 | Matsuura |

(56) References Cited

U.S. PATENT DOCUMENTS

| | | |
|---|---|---|
| 4,840,187 A | 6/1989 | Brazier |
| 4,863,449 A | 9/1989 | Therriault et al. |
| 4,865,026 A | 9/1989 | Barrett |
| 4,872,450 A | 10/1989 | Austad |
| 4,878,901 A | 11/1989 | Sachse |
| 4,897,081 A | 1/1990 | Poirier et al. |
| 4,902,565 A | 2/1990 | Brook |
| 4,906,233 A | 3/1990 | Moriuchi et al. |
| 4,906,240 A | 3/1990 | Reed et al. |
| 4,917,112 A | 4/1990 | Kalt |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,000,741 A | 3/1991 | Kalt |
| 5,018,515 A | 5/1991 | Gilman |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,106,629 A | 4/1992 | Cartmell et al. |
| 5,134,994 A | 8/1992 | Say |
| 5,149,331 A | 9/1992 | Ferdman et al. |
| 5,160,315 A | 11/1992 | Heinecke et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,306,798 A | 4/1994 | Horn et al. |
| 5,342,376 A | 8/1994 | Ruff |
| 5,344,415 A | 9/1994 | DeBusk et al. |
| 5,358,494 A | 10/1994 | Svedman |
| 5,376,067 A | 12/1994 | Daneshvar |
| 5,380,294 A | 1/1995 | Persson |
| 5,423,737 A | 6/1995 | Cartmell et al. |
| 5,429,593 A | 7/1995 | Matory |
| 5,435,009 A | 7/1995 | Schild et al. |
| 5,437,622 A | 8/1995 | Carion |
| 5,437,651 A | 8/1995 | Todd et al. |
| 5,489,262 A | 2/1996 | Cartmell et al. |
| 5,497,788 A | 3/1996 | Inman et al. |
| 5,520,629 A | 5/1996 | Heinecke et al. |
| 5,527,293 A | 6/1996 | Zamierowski |
| 5,538,502 A | 7/1996 | Johnstone |
| 5,549,584 A | 8/1996 | Gross |
| 5,556,375 A | 9/1996 | Ewall |
| 5,607,388 A | 3/1997 | Ewall |
| 5,628,230 A | 5/1997 | Flam |
| 5,636,643 A | 6/1997 | Argenta et al. |
| 5,645,081 A | 7/1997 | Argenta et al. |
| 5,653,244 A | 8/1997 | Shaw |
| 5,714,225 A | 2/1998 | Hansen et al. |
| 5,792,088 A | 8/1998 | Felder et al. |
| 5,844,013 A | 12/1998 | Kenndoff et al. |
| 5,866,249 A | 2/1999 | Yarusso et al. |
| 5,944,017 A | 8/1999 | Tweedle |
| 5,950,238 A | 9/1999 | Klein |
| 5,973,221 A | 10/1999 | Collyer et al. |
| 6,071,267 A | 6/2000 | Zamierowski |
| 6,086,450 A | 7/2000 | Mankovitz |
| 6,109,267 A | 8/2000 | Shaw et al. |
| 6,135,116 A | 10/2000 | Vogel et al. |
| 6,162,960 A | 12/2000 | Klein |
| 6,176,868 B1 | 1/2001 | Detour |
| 6,213,840 B1 | 4/2001 | Han |
| 6,241,747 B1 | 6/2001 | Ruff |
| 6,270,910 B1 | 8/2001 | Jaeger et al. |
| 6,287,316 B1 | 9/2001 | Agarwal et al. |
| 6,345,623 B1 | 2/2002 | Heaton et al. |
| 6,361,397 B1 | 3/2002 | Mankovitz et al. |
| 6,420,622 B1 | 7/2002 | Johnston et al. |
| 6,440,093 B1 | 8/2002 | McEwen et al. |
| 6,458,109 B1 | 10/2002 | Henley et al. |
| 6,488,643 B1 | 12/2002 | Tumey et al. |
| 6,493,568 B1 | 12/2002 | Bell et al. |
| 6,500,112 B1 | 12/2002 | Khouri |
| 6,528,697 B1 | 3/2003 | Knutson et al. |
| 6,553,998 B2 | 4/2003 | Heaton et al. |
| 6,566,576 B1 | 5/2003 | Komerska et al. |
| 6,648,862 B2 | 11/2003 | Watson |
| 6,685,681 B2 | 2/2004 | Lockwood et al. |
| 6,752,794 B2 | 6/2004 | Lockwood et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,867,342 B2 | 3/2005 | Johnston et al. |
| D503,509 S | 4/2005 | Bell et al. |
| 6,936,037 B2 | 8/2005 | Bubb et al. |
| 6,951,553 B2 | 10/2005 | Bubb et al. |
| 7,004,915 B2 | 2/2006 | Boynton et al. |
| 7,070,584 B2 | 7/2006 | Johnson et al. |
| 7,090,647 B2 | 8/2006 | Mimura et al. |
| 7,135,007 B2 | 11/2006 | Scott et al. |
| 7,144,294 B2 | 12/2006 | Bell et al. |
| 7,195,624 B2 | 3/2007 | Lockwood et al. |
| 7,201,063 B2 | 4/2007 | Taylor |
| 7,201,263 B2 | 4/2007 | Osada et al. |
| 7,214,202 B1 | 5/2007 | Vogel et al. |
| 7,316,672 B1 | 1/2008 | Hunt et al. |
| 7,338,482 B2 | 3/2008 | Lockwood et al. |
| 7,361,184 B2 | 4/2008 | Joshi |
| 7,381,859 B2 | 6/2008 | Hunt et al. |
| 7,455,681 B2 | 11/2008 | Wilke et al. |
| 7,504,549 B2 | 3/2009 | Castellani et al. |
| 7,520,872 B2 | 4/2009 | Biggie et al. |
| 7,532,953 B2 | 5/2009 | Vogel |
| 7,534,927 B2 | 5/2009 | Lockwood et al. |
| 7,569,742 B2 | 8/2009 | Haggstrom et al. |
| 7,699,831 B2 | 4/2010 | Bengtson et al. |
| 7,700,819 B2 | 4/2010 | Ambrosio et al. |
| 7,846,141 B2 | 12/2010 | Weston |
| 8,062,273 B2 | 11/2011 | Weston |
| 8,100,848 B2 | 1/2012 | Wilkes et al. |
| 8,129,580 B2 | 3/2012 | Wilkes et al. |
| 8,216,198 B2 | 7/2012 | Heagle et al. |
| 8,241,261 B2 | 8/2012 | Randolph et al. |
| 8,251,979 B2 | 8/2012 | Malhi |
| 8,257,327 B2 | 9/2012 | Blott et al. |
| 8,398,614 B2 | 3/2013 | Blott et al. |
| 8,399,730 B2 | 3/2013 | Kazala, Jr. et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,641,691 B2 | 2/2014 | Fink et al. |
| 8,679,081 B2 | 3/2014 | Heagle et al. |
| 8,722,959 B2 | 5/2014 | Wilkes et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,095,468 B2 | 8/2015 | Kazala, Jr. et al. |
| 9,198,801 B2 | 12/2015 | Weston |
| 9,211,365 B2 | 12/2015 | Weston |
| 9,289,542 B2 | 3/2016 | Blott et al. |
| 9,572,719 B2 | 2/2017 | Long et al. |
| 9,750,641 B2 | 9/2017 | Kazala, Jr. et al. |
| 10,143,593 B2 | 12/2018 | Kazala, Jr. et al. |
| 10,568,768 B2 * | 2/2020 | Long ............... A61M 1/90 |
| 2001/0029956 A1 | 10/2001 | Argenta et al. |
| 2001/0043943 A1 | 11/2001 | Coffey |
| 2002/0007014 A1 | 1/2002 | Hyde et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0040691 A1 | 2/2003 | Griesbach et al. |
| 2003/0109816 A1 | 6/2003 | Lachenbruch et al. |
| 2003/0139697 A1 | 7/2003 | Gilman |

(56) References Cited

U.S. PATENT DOCUMENTS

| | | |
|---|---|---|
| 2003/0212359 A1 | 11/2003 | Butler |
| 2004/0006319 A1 | 1/2004 | Lina et al. |
| 2004/0030304 A1 | 2/2004 | Hunt et al. |
| 2004/0039415 A1 | 2/2004 | Zamierowski |
| 2004/0064111 A1 | 4/2004 | Lockwood et al. |
| 2004/0064132 A1 | 4/2004 | Boehringer et al. |
| 2004/0127836 A1 | 7/2004 | Sigurjonsson et al. |
| 2004/0242119 A1 | 12/2004 | Francis |
| 2004/0243073 A1 | 12/2004 | Lockwood et al. |
| 2005/0059918 A1 | 3/2005 | Sigurjonsson et al. |
| 2005/0070858 A1 | 3/2005 | Lockwood et al. |
| 2005/0101940 A1 | 5/2005 | Radl et al. |
| 2005/0142331 A1 | 6/2005 | Anderson et al. |
| 2005/0209574 A1 | 9/2005 | Boehringer et al. |
| 2005/0222544 A1 | 10/2005 | Weston |
| 2005/0228329 A1 | 10/2005 | Boehringer et al. |
| 2006/0041247 A1 | 2/2006 | Petrosenko et al. |
| 2006/0064049 A1 | 3/2006 | Marcussen |
| 2006/0079852 A1 | 4/2006 | Bubb et al. |
| 2006/0149171 A1 | 7/2006 | Vogel et al. |
| 2006/0173253 A1 | 8/2006 | Ganapathy et al. |
| 2006/0189910 A1 | 8/2006 | Johnson et al. |
| 2006/0213527 A1 | 9/2006 | Argenta et al. |
| 2006/0264796 A1 | 11/2006 | Flick et al. |
| 2007/0021697 A1 | 1/2007 | Ginther et al. |
| 2007/0027414 A1 | 2/2007 | Hoffman et al. |
| 2007/0032755 A1 | 2/2007 | Walsh |
| 2007/0044801 A1 | 3/2007 | Mathis et al. |
| 2007/0066946 A1 | 3/2007 | Haggstrom et al. |
| 2007/0078366 A1 | 4/2007 | Haggstrom et al. |
| 2007/0129707 A1 | 6/2007 | Blott et al. |
| 2007/0135777 A1 | 6/2007 | Greene et al. |
| 2007/0167884 A1 | 7/2007 | Mangrum et al. |
| 2007/0185426 A1 | 8/2007 | Ambrosio et al. |
| 2007/0185463 A1 | 8/2007 | Mulligan |
| 2007/0219497 A1 | 9/2007 | Johnson et al. |
| 2007/0219513 A1 | 9/2007 | Lina et al. |
| 2007/0219532 A1 | 9/2007 | Karpowicz et al. |
| 2007/0225663 A1 | 9/2007 | Watt et al. |
| 2007/0255193 A1 | 11/2007 | Patel et al. |
| 2008/0004549 A1 | 1/2008 | Anderson et al. |
| 2008/0009812 A1 | 1/2008 | Riesinger |
| 2008/0026023 A1 | 1/2008 | Tauer et al. |
| 2008/0039763 A1 | 2/2008 | Sigurjonsson et al. |
| 2008/0071207 A1 | 3/2008 | de Luis et al. |
| 2008/0071214 A1 | 3/2008 | Locke et al. |
| 2008/0076844 A1 | 3/2008 | Van Sumeren et al. |
| 2008/0103462 A1 | 5/2008 | Wenzel et al. |
| 2008/0103489 A1 | 5/2008 | Dahners |
| 2008/0119802 A1 | 5/2008 | Riesinger |
| 2009/0043268 A1 | 2/2009 | Eddy et al. |
| 2009/0047855 A1 | 2/2009 | Seth et al. |
| 2009/0125004 A1 | 5/2009 | Shen et al. |
| 2009/0177051 A1 | 7/2009 | Arons et al. |
| 2009/0204084 A1 | 8/2009 | Blott et al. |
| 2009/0204085 A1 | 8/2009 | Biggie et al. |
| 2009/0227968 A1 | 9/2009 | Vess |
| 2009/0234307 A1 | 9/2009 | Vitaris |
| 2009/0264807 A1 | 10/2009 | Haggstrom et al. |
| 2009/0293887 A1 | 12/2009 | Wilkes et al. |
| 2009/0299257 A1 | 12/2009 | Long et al. |
| 2012/0220963 A1 | 8/2012 | Hunt et al. |
| 2014/0163491 A1 | 6/2014 | Schuessler et al. |
| 2015/0080788 A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| CA | 2468309 A1 | 7/2003 |
| CA | 2560068 A1 | 10/2005 |
| CA | 2651833 A1 | 11/2007 |
| CN | 1545991 A | 11/2004 |
| CN | 101277734 A | 10/2008 |
| DE | 26 40 413 A1 | 3/1978 |
| DE | 39 07 522 C1 | 4/1990 |
| DE | 43 06 478 A1 | 9/1994 |
| DE | 29 504 378 U1 | 9/1995 |
| DE | 20 2006 007877 U1 | 7/2006 |
| DE | 102005007016 A1 | 8/2006 |
| EP | 0100148 A1 | 2/1984 |
| EP | 0117632 A2 | 9/1984 |
| EP | 0161865 A2 | 11/1985 |
| EP | 0330373 A2 | 8/1989 |
| EP | 0358302 A2 | 3/1990 |
| EP | 0421465 A2 | 4/1991 |
| EP | 0424165 A1 | 4/1991 |
| EP | 0691113 A1 | 1/1996 |
| EP | 0756854 A1 | 2/1997 |
| EP | 1018967 A1 | 7/2000 |
| EP | 2282788 B1 | 12/2016 |
| FR | 1163907 A | 10/1958 |
| FR | 2661821 A1 | 11/1991 |
| GB | 692578 A | 6/1953 |
| GB | 1574066 A | 9/1980 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | H08154964 A | 6/1996 |
| JP | H10356 A | 1/1998 |
| JP | 2000-189427 A | 7/2000 |
| JP | 2000210386 A | 8/2000 |
| JP | 2002-078730 A | 3/2002 |
| JP | 2003-116907 A | 4/2003 |
| JP | 2004-160220 A | 6/2004 |
| JP | 2006-141908 A | 6/2006 |
| JP | 2006219776 A | 8/2006 |
| JP | 2006239213 A | 9/2006 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 92/05755 A1 | 4/1992 |
| WO | 1993/000056 A1 | 1/1993 |
| WO | 93/009727 A1 | 5/1993 |
| WO | 199415562 A1 | 7/1994 |
| WO | 94/20041 A1 | 9/1994 |
| WO | 199420152 A1 | 9/1994 |
| WO | 1995/14451 A1 | 6/1995 |
| WO | 96/05873 A1 | 2/1996 |
| WO | 1997005838 A1 | 2/1997 |
| WO | 1997/11658 A1 | 4/1997 |
| WO | 97/18007 A1 | 5/1997 |
| WO | 99/01173 A1 | 1/1999 |
| WO | 99/13793 A1 | 3/1999 |
| WO | 0007653 A1 | 2/2000 |
| WO | 2000061206 A1 | 10/2000 |
| WO | 2001/02478 A1 | 1/2001 |
| WO | 01/034223 A1 | 5/2001 |
| WO | 2001/89431 A1 | 11/2001 |
| WO | 200185248 A1 | 11/2001 |
| WO | 2002/20067 A2 | 3/2002 |
| WO | 2002/083046 A1 | 10/2002 |
| WO | 2003017898 A1 | 3/2003 |
| WO | 2003/057071 A2 | 7/2003 |
| WO | 2003/057307 A1 | 7/2003 |
| WO | 2003077989 A1 | 9/2003 |
| WO | 2003/086262 A1 | 10/2003 |
| WO | 2003101385 A2 | 12/2003 |
| WO | 2004/047695 A1 | 6/2004 |
| WO | 2004/060413 A1 | 7/2004 |
| WO | 2005025447 A2 | 3/2005 |
| WO | 2005034797 A2 | 4/2005 |
| WO | 2005051461 A1 | 6/2005 |
| WO | 2005082435 A1 | 9/2005 |
| WO | 2005/091884 A2 | 10/2005 |
| WO | 2005/123170 A1 | 12/2005 |
| WO | 2006/012745 A1 | 2/2006 |
| WO | 2007030599 A2 | 3/2007 |
| WO | 2007031762 A1 | 3/2007 |

(56) References Cited

FOREIGN PATENT DOCUMENTS

| | | |
|---|---|---|
| WO | 2007033679 A2 | 3/2007 |
| WO | 2007/041642 A2 | 4/2007 |
| WO | 2007085396 A1 | 8/2007 |
| WO | 2007/120138 A2 | 10/2007 |
| WO | 2008013869 A2 | 1/2008 |
| WO | 2008013896 A2 | 1/2008 |
| WO | 2008/020209 A2 | 2/2008 |
| WO | 2008041926 A1 | 4/2008 |
| WO | 2008054312 A1 | 5/2008 |
| WO | 2008063281 A2 | 5/2008 |
| WO | 2008/104609 A1 | 9/2008 |
| WO | 2009019496 A2 | 2/2009 |
| WO | 2009/047524 A2 | 4/2009 |
| WO | 2009/071926 A1 | 6/2009 |

OTHER PUBLICATIONS

A. Dee, "The successful management of a dehisced surgical wound with TNP following Femoropopliteal bypass", Journal of Wound Care, vol. 16, No. 1, Jan. 2007.
Ogazon, Use of Vacuum-Assisted Closure in the Treatment of Surgical Infection Sites Cir. Mar.-Apr. 2006; 74(2): 107-13 (Spanish).
Timmenga, "The Effects of Mechanical Stress on Healing Skin Wounds: An Experimental Study in Rabbits Using Tissues Expansions," British Journal of Plastic Surgery 1991; 44(7): 514-519.
Cunningham "Development of in-vitro Model to Simulate Dermal Wound Bed Interaction with GranuFoam and Gauze Dressing under Sub Atmospheric Pressure" RPT 111-05-02, Device Implant Innovations 2006.
Delalleau, A., et al, "Characterization of the Mechanical Properties of Skin by Inverse Analysis Combined with the Indentation Test" Journal of Biomechanics, 2006; pp. 1603-1610.
Pailler-Mattei, C., "Caracte; Risation Me' Canique et Tribologizue de la Peau Humain In Vivo", 2004-31.
Khatyr, F., "Model of the Viscoelastic Behavior of Skin In Vivo and Study of Anisotropy", Skin Research and Technology 2004; pp. 96-103.
Wilkes, "3D Strain Measurement in Soft Tissue: Demonstration of a Novel Inverse Finite Element Model Algorithm on MicroCT Images of a Tissue Phantom Exposed to Negative Pressure Wound Therapy," Journal of the Mechanical Behavior of Biomedical Materials (2008), pp. 1-16.
Diridollou, "In vivo Model of the Mechanical Properties of the Human Skin under Suction", Skin Research and Technology, 2000; 6:214-221.
Woo, "Structural Model to Describe the Non-Linear Stress-Strain Behavior for Parallel-Fibered Collagenous Tissues," Journal of Biomechanical Engineering, Nov. 1989, vol. 111/361.
International Search Report and Written Opinion dated Oct. 20, 2009; PCT International Application No. PCT/US2009/045747.
International Search Report and Written Opinion dated Oct. 16, 2009; PCT International Application No. PCT/US2009/045752.
International Search Report and Written Opinion dated Oct. 26, 2009; PCT International Application No. PCT/US2009/045751.
International Search Report and Written Opinion dated Oct. 27, 2009; PCT International Application No. PCT/US2009/045744.
International Search Report and Written Opinion dated Oct. 14, 2009; PCT International Application No. PCT/US2009/045746.
International Search Report and Written Opinion dated Nov. 11, 2009; PCT International Application No. PCT/US2009/045754.
International Search Report and Written Opinion dated Oct. 21, 2009; PCT International Application No. PCT/US2009/045749.
International Search Report and Written Opinion dated Nov. 12, 2009; PCT International Application No. PCT/US2009/045753.
International Search Report and Written Opinion dated Feb. 25, 2010; PCT International Application No. PCT/US2009/045750.
International Search Report and Written Opinion dated Mar. 12, 2010; PCT International Application No. PCT/US2009/045755.

Product Information for OptSiteTM dressing. Accessed Aug. 14, 2011.
International Search Report and Written Opinion dated Aug. 30, 2011 for PCT International Application No. PCT/US2011/034300.
Examination Report for corresponding EP 09770659.2, dated Sep. 4, 2013.
International Search Report and Written Opinion dated Aug. 20, 2009; PCT International Application No. PCT/US2009/045743.
European Search Report for EP 09770665.9, dated Feb. 25, 2015.
Canadian Examiner's Report for Corresponding Application No. 2980359, dated Jul. 31, 2018.
A Prospective, Blinded, Randomized, Controlled Clinical Trial of Topical Negative Pressure Use in Skin Grafting, Elias Moisidis, Tim Heath, Catherine Boorer, Kevin Ho, Anand K. Deva, Sydney, Australia, From the Department of Plastic and Maxillofacial Surgery, Liverpool Hospital. Received for publication Mar. 25, 2003; revised Oct. 1, 2003.
The Vacuum Assisted Closure Device, A Method of Securing Skin Grafts and Improving Grafts Survival; Lynette A. Scherer, MD; Stephen Shiver, MD; Michael Chang, MD; J_ Wayne Meredith, MD; John T. Owings. MD; From the Departments of Surgery, University of California—Davis Medical Center, Sacramento (Ors. Sherer and Owings), and Wake Forest University Baptist Medical Center, Winston-Salem, NC (Ors. Shiver, Chang, and Meredith); Arch SurQNol 137, AuQ 2002; www.archsurQ.com.
Extended European Search Report corresponding to Application No. 171645070, dated Jul. 18, 2017.
Extended European Search Report for corresponding Eurpean Application No. 12171212.9 dated Nov. 14, 2012.
European Search Report for EP 14182278.3 dated Jan. 7, 2015.
European Examination Report for corresponding EP09770663.4, dated Aug. 9, 2013.
Chintamani V.S. et al. : "Half Versus Full Vacuum Suction Drainage After Modified Radical Mastectomy for Breast Cancer—a Prospective Randomized Clinical Trial [ISRCTN24484328]", BMC Cancer, 2005, vol. 5, article 11; abstract.
Japanese Office Action corresponding to Application No. 2016104769, dated Mar. 7, 2017.
European Search Report for corresponding Application No. 16171527.1 dated Dec. 9, 2016.
Communication pursuant to Rule 114(2) EPC for corresponding EP Application 09770664.2, dated Aug. 22, 2013.
Canadian Office Action dated May 25, 2016, corresponding to Canada Application No. 2,725,945.
Mexican Office Action corresponding to Application No. MX/a/2010/013134, dated Oct. 26, 2017.
Indian Examination Report for corresponding Application No. 9029/DELNP/2010, dated Nov. 23, 2017.
Extended European Search Report for corresponding Application No. 161998968, dated Mar. 1, 2017.
Japanese Notice of Rejection Corresponding to Application No. 2017-235283, dated Aug. 6, 2019.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

(56) References Cited

OTHER PUBLICATIONS

Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., JR., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. YU.N., et al; "Active Wound Drainage", Vestnki Khirurgi, vol. 138, Issue 4, 1987, and 7 page English translation thereof.
Davydov, YU.A., et al; "Bacteriological and Cytological Assessment of Vacuum Therapy for Purulent Wounds"; Vestnik Khirugi, Oct. 1988, pp. 48-52, and 8 page English translation thereof.
Davydov, YU.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax,"Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Japanese Notice of Rejection for corresponding Application No. 2020-005250, dated Oct. 27, 2020.

* cited by examiner

REDUCED-PRESSURE SURGICAL WOUND TREATMENT SYSTEMS AND METHODS

RELATED APPLICATIONS

This application is a continuation of U.S. patent application Ser. No. 15/411,395, entitled "Reduced-Pressure Surgical Wound Treatment Systems and Methods," filed Jan. 20, 2017, which is a continuation of U.S. patent application Ser. No. 12/475,398, now U.S. Pat. No. 9,572,719, entitled "Reduced-Pressure Surgical Wound Treatment Systems and Methods," filed May 29, 2009, which claims the benefit, under 35 USC § 119(e), of the filing of U.S. Provisional Patent Application No. 61/057,807, entitled "Reduced-Pressure Surgical Wound Treatment System," filed May 30, 2008; U.S. Provisional Patent Application No. 61/057,798, entitled "Dressing Assembly For Subcutaneous Wound Treatment Using Reduce Pressure," filed May 30, 2008; U.S. Provisional Patent Application No. 61/057,808, entitled "See-Through, Reduced-Pressure Dressing," filed May 30, 2008; U.S. Provisional Patent Application No. 61/057,802, entitled "Reduced-Pressure Dressing Assembly For Use in Applying a Closing Force," filed May 30, 2008; U.S. Provisional Patent Application No. 61/057,803, entitled "Reduced-Pressure, Linear-Wound Treatment System," filed May 30, 2008; U.S. Provisional Patent Application No. 61/057,800, entitled "Reduced-Pressure, Compression System and Apparatus for use on a Curved Body Part," filed, May 30, 2008; U.S. Provisional Patent Application No. 61/057,797, entitled "Reduced-Pressure, Compression System and Apparatus for Use on Breast Tissue," filed May 30, 2008; U.S. Provisional Patent Application No. 61/057,805, entitled "Super-Absorbent, Reduced-Pressure Wound Dressing and System," filed May 30, 2008; U.S. Provisional Patent Application No. 61/057,810, entitled "Reduced-Pressure, Compression System and Apparatus for Use on a Joint," filed May 30, 2008; U.S. Provisional Patent Application No. 61/121,362, entitled "Reduced-Pressure Wound Treatment System Employing an Anisotropic Drape," filed Dec. 10, 2008; and U.S. Provisional Patent Application No. 61/144,067, entitled "Reduced-Pressure, Compression System and Apparatus for Use on a Joint," filed Jan. 12, 2009, the entire contents of which are incorporated by reference herein.

BACKGROUND

The present invention relates generally to medical treatment systems, and more particularly, to reduced-pressure wound treatment systems suitable for use with surgical wounds and other tissue sites.

Physicians perform millions of surgical procedures each year around the world. Many of the procedures are performed as open surgery and an increasing number are performed using minimally invasive surgery, such as endoscopic, arthroscopic, and laparoscopic procedures. As one example, the American Society for Aesthetic Plastic Surgery reports that there were more than 450,000 liposuction procedures in the United States in 2007.

Surgical procedures involve acute wounds, e.g., an incision, in the skin and related tissue. In many instances, the incision is closed at the conclusion of the procedure using a mechanical apparatus, such as staples or suture, or closed using adhesives. Thereafter, the wound is often merely covered with a dry, sterile bandage. Of course, there is usually more disruption than just at the epidermis.

With many surgical procedures, particularly those done with minimally invasive techniques, much of the disruption or damage is below the epidermis, or at a subcutaneous level. Again, as one example, in one type of liposuction procedure, after the introduction of a tumescent fluid (saline, mild painkiller, and epinephrine), the surgeon will use a trocar and cannula with suction to remove fatty areas. In doing so, it is not uncommon to have subcutaneous voids and other tissue defects formed at tissue sites remote from the incision through which the cannula was placed or other incisions through which equipment was placed. The damaged tissue will need time and care to heal and poses a number of potential complications and risks including edema, seroma, hematoma, further bruising, and ecchymosis to name some.

BRIEF SUMMARY

Shortcomings with devices, systems, and methods for post-surgical wound care at the incision and at the damaged subcutaneous tissue are addressed by the illustrative embodiments herein. According to one illustrative embodiment, a reduced-pressure system for treating subcutaneous damaged tissue includes a shaped dressing bolster having an oblique extremity and formed from a medical bolster material. The shaped dressing bolster is for placing on the patient's epidermis and is substantially sized to overlay the damaged subcutaneous tissue. The reduced-pressure system further includes an over-drape for providing a fluid seal over the shaped dressing bolster and a portion of the patient's epidermis; a reduced-pressure source; and a reduced-pressure interface. The reduced-pressure interface is for delivering reduced pressure to the shaped dressing bolster. The system further includes a reduced-pressure delivery conduit for fluidly coupling the reduced-pressure source and the reduced-pressure interface. The shaped dressing bolster has a characteristic of generating and evenly distributing a compressive force when placed under reduced pressure. A closing force may also be generated as part of the characteristic of the shaped dressing bolster.

According to another illustrative embodiment, a reduced-pressure system for treating damaged subcutaneous tissue in a peri-incisional region of a patient after a surgical procedure includes a shaped dressing bolster for deploying on the patient's epidermis and that is substantially sized to overlay the damaged subcutaneous tissue and an associated incision. The shaped dressing bolster includes a medical bolster material having a shaped extremity operable to evenly distribute a force. The shaped dressing bolster has a first surface and a second, inward-facing surface. The shaped extremity includes a medical bolster material having an oblique surface. The reduced-pressure system further includes sealing subsystem for providing a fluid seal over the shaped dressing bolster and a portion of the patient's epidermis and a reduced-pressure subsystem operable to deliver reduced pressure to the sealing subsystem. The system also includes an inner layer having a first surface and a second, inward-facing surface, and formed with a treatment-area aperture. The first surface of the inner layer may be coupled at least in part to the second surface of the shaped dressing bolster. The shaped dressing bolster, sealing subsystem, and reduced-pressure subsystem are operable to develop a compressive force realized at a tissue site deeper than the epidermis and an inward force directed toward the incision and substantially within the plane of the epidermis.

According to another illustrative embodiment, a method of manufacturing a reduced-pressure system for treating damaged subcutaneous tissue includes the steps of providing a medical bolster material and shaping the medical bolster material to form a shaped dressing bolster, having first surface and a second, inward-facing surface, for placing on the patient's epidermis. The step of shaping the medical bolster material includes shaping the medical bolster material so that the shaped dressing bolster has a an oblique extremity. The method further includes providing an over-drape; and providing a sealing apparatus. The sealing apparatus is operable to couple to at least a portion of the second surface of the over-drape. The sealing apparatus is also operable to form a fluid seal between a patient's epidermis and the over-drape when in use. The method also involves providing a reduced-pressure delivery conduit.

According to another illustrative embodiment, a reduced-pressure system for treating a tissue site includes a directed-force member having an oblique edge for evenly distributing a compressive force when placed under reduced-pressure. The directed-force member is formed with a plurality of channels for transmitting a fluid. The reduced-pressure system also includes a drape for providing a fluid seal over at least a portion of the directed-force member and a patient's epidermis and includes a reduced-pressure conduit for fluidly coupling a reduced-pressure source and the directed-force member.

According to another illustrative embodiment, a reduced-pressure system for treating subcutaneous damaged tissue includes a shaped dressing bolster having an oblique extremity and formed from a medical bolster material. The shaped dressing bolster is for placing on the patient's epidermis and is sized to substantially overlay the damaged subcutaneous tissue. The reduced-pressure system further includes an over-drape for providing a fluid seal over the shaped dressing bolster and a portion of the patient's epidermis. The system also includes a reduced-pressure interface coupled to the drape and a reduced-pressure source. The reduced-pressure interface is for delivering reduced pressure to the shaped dressing bolster. The system includes a reduced-pressure delivery conduit for fluidly coupling the reduced-pressure source and the reduced-pressure interface. In cross-section, the shaped dressing bolster has a top surface, a first side surface, and a second side surface. The over-drape contacts the top surface, the first side, and the second side.

According to still another illustrative embodiment, a method of treating a damaged subcutaneous tissue on a patient includes the step of positioning a shaped dressing bolster over the damaged subcutaneous tissue. The shaped dressing bolster has an oblique extremity and is formed from a medical bolster material. The method further includes deploying an over-drape over the shaped dressing bolster and a portion of the patient's epidermis to provide a fluid seal and providing a reduced-pressure source. The method further includes coupling a reduced-pressure interface to the drape; fluidly coupling a reduced-pressure delivery conduit to the reduced-pressure source and to the reduced-pressure interface; and activating the reduced-pressure source to provide reduced pressure to the shaped dressing bolster to develop a compressive force and a closing force.

Other features and advantages of the illustrative embodiments will become apparent with reference to the drawings and the detailed description that follow.

BRIEF DESCRIPTION OF THE DRAWINGS

A more complete understanding of the present invention may be obtained by reference to the following Detailed Description when taken in conjunction with the accompanying Drawings wherein.

DETAILED DESCRIPTION

In the following detailed description of the preferred embodiments, reference is made to the accompanying drawings that form a part hereof, and in which is shown, by way of illustration, specific embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

Figure 1:
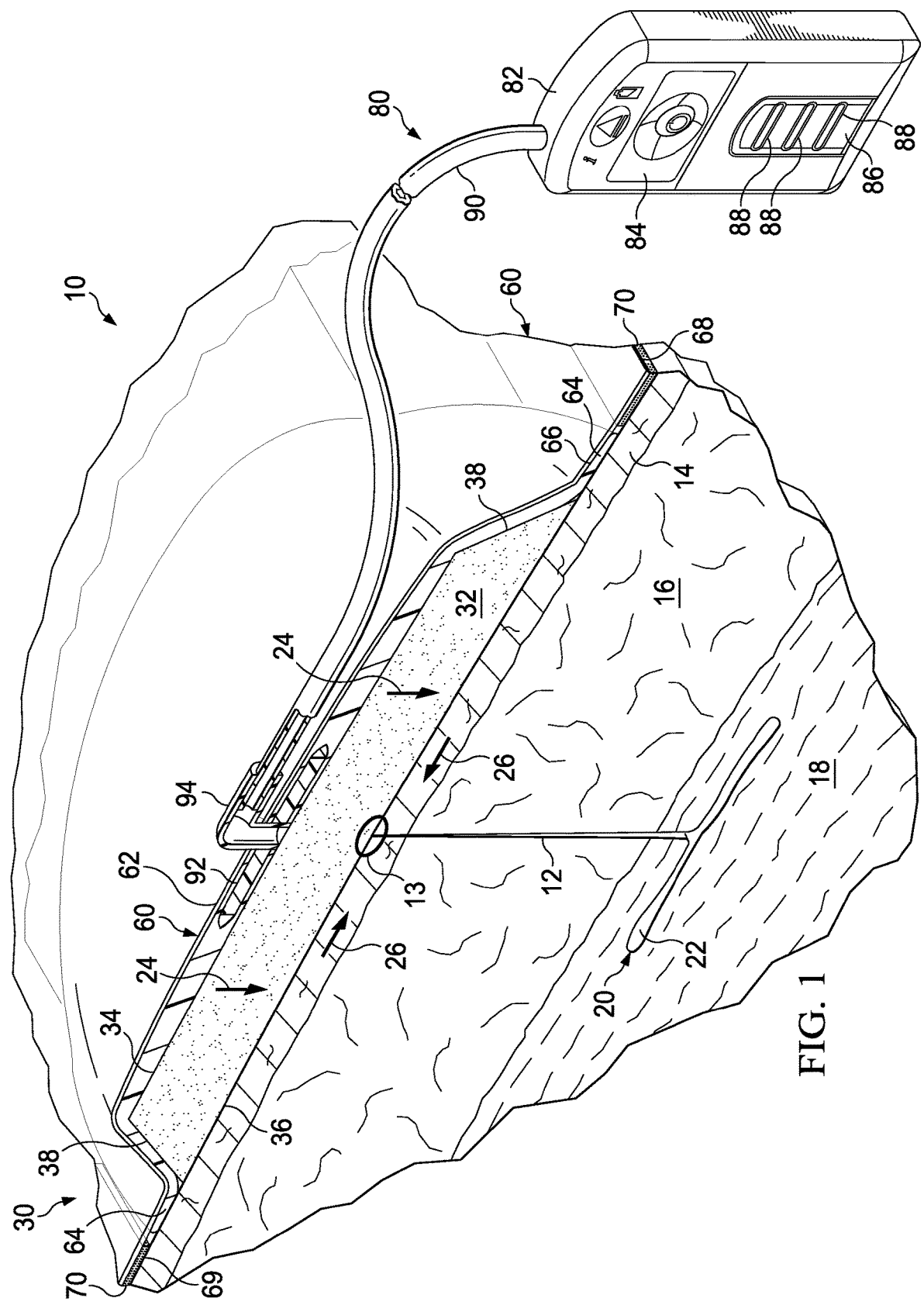
FIG. 1 is a schematic, perspective view of an illustrative embodiment of a reduced-pressure surgical wound treatment system shown over an incision and above damaged subcutaneous tissue.

Referring now to FIG. 1, a reduced-pressure system 10 for treating tissue, such as subcutaneous tissue in a peri-incisional region or an incision, according to one illustrative embodiment is shown. As used herein, "or" does not require mutual exclusivity. The reduced-pressure system 10 is shown in a peri-incisional region around an incision 12, which is through epidermis 14, or skin, and dermis 16 and reaching into a hypodermis, or subcutaneous tissue 18. The subcutaneous tissue 18 may include numerous tissue types, such as fatty tissue or muscle. A damaged, or undermined or abnormal, subcutaneous tissue site 20 is shown extending from the incision 12 and includes, in this instance, a subcutaneous defect, dead space, or void 22.

The damaged subcutaneous tissue 20 may have been caused by a surgical procedure, such as liposuction. The damaged subcutaneous tissue 20 may include voids, such as the void 22, open spaces, or various defects that can be troublesome for a number of reasons such as allowing fluids to build that may result in edema. The term "fluid" as used herein generally refers to gas or liquid, but may also include any other flowable material, including but not limited to gels, colloids, and foams.

The system 100 may help the damaged subcutaneous tissue 20 to be approximated—brought together or near—to improve healing while minimizing or eliminating skin irritation. The system 100 may also develop a closing force directed toward the incision 12 and that may help hold the incision closed or provide support. The system 100 may help minimize shear stress on deep wounds, e.g., void 22. The system 100 may also help the incision 12 remain dry, help avoid dead space formation, improve perfusion, and avoid seroma and hematoma formation. In addition, system 100 may help minimize bruising and edema secondary to certain surgical procedures. The system 100 may provide comfort for the patient and a relatively shortened duration that the system 100 may be required on the patient. With the system 100, dressing changes may be eliminated or the number of required changes minimized.

The incision 12 may be closed using any mechanical closing means such as staples or sutures, or may be closed using an adhesive, but is shown in this illustrative embodiment as being closed with suture 13. The reduced-pressure system 10 typically is for treating an area and, in particular, is typically for treating a subcutaneous tissue site 20 and the tissue around subcutaneous tissue 20, but the reduced-pressure system 10 may also be used to treat a more limited area around the incision 12.

The reduced-pressure system 10 includes a dressing assembly 30, which includes a shaped dressing bolster 32, a sealing subsystem 60, and a reduced-pressure subsystem 80. The reduced-pressure system 10 develops a force, which may include a vertical force or a closing force. As used in this context and herein, "vertical" means parallel to arrows 24 irrespective of orientation but shown vertically in FIG. 1. The developed force in the vertical may be a compressive force or a lifting force. In the illustrative embodiment, the net vertical force is presented as a compressive force represented by the arrow 24, and the closing force is shown by arrows 26. The compressive force 24 may realized at the subcutaneous tissue 20 or deeper, including at an organ. As used herein subcutaneous tissue may include the deeper tissues as well. The compressive force 24 may be directed vertically (i.e., generally toward a center line of patient's body or a body portion or with reference to the shaped dressing bolster 32 from the first side 34 to the second side 34. The compressive force 24 may reach subcutaneous tissues. The magnitude of the vertical force 24 may be influenced by the size and shape of the shaped dressing bolster 32.

In some situations, it may be desirable to have the shaped dressing bolster 32 deliver the vertical force as a lifting force. The density and thickness of the shaped dressing bolster 32 are variables for controlling lifting. For example, if the density of a medical bolster material is less than the density of the tissue, e.g., epidermis, at the tissue site, a lifting force may be generated. As a substantially thick portion of a shaped dressing bolster 32 experiences reduced pressure, the shaped dressing bolster contracts toward a central portion from all directions. The portion of the shaped dressing bolster 32 near the patient's epidermis will pull away from the patient's epidermis since the central portion is above the patient's epidermis. This creates a vertical lifting force. A portion of the shaped dressing bolster may provide a compressive force, while another portion—generally a central portion—provides a lifting force with respect to the patient or the system.

The illustrative embodiment of FIG. 1 is presented with the vertical force applying a compressive force 24. As described further below, the shaped dressing bolster 32 may be shaped and configured to allow the compressive force to be distributed fairly evenly over the patient's epidermis 14 and beneath the epidermis 14. Otherwise, if there are areas of substantially increased force as compared to other areas, skin irritation may result. The reduced-pressure system 10 may also be operable to develop the closing force, i.e. a substantially tangential force towards an interior portion of the dressing assembly 30, represented by the reference numerals 26. The closing force 26 remains substantially within the plane of the epidermis 14; in other words, the closing force 26 operates mainly within the epidermis 14. In addition, the reduced-pressure system 10 is operable to deliver reduced pressure to the incision 12 that, depending on the incision and the state of healing, may be realized at the level of the subcutaneous void 22 to help approximate—bring together—the tissues in that region as well as to help remove any air or any other fluids or provide reduced-pressure therapy. The compressive force 24 may also close or help close the void 22.

As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Unless otherwise indicated, values of pressure stated herein are gauge pressures. The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure.

The dressing assembly 30 includes the shaped dressing bolster 32 that has a first side 34 and a second, inward (skin-facing or patient-facing) side 36. The shaped dressing bolster 32 may be sized and shaped to substantially match the estimated area of damaged subcutaneous tissue 20 although a larger or smaller size may be used in different applications. The shaped dressing bolster 32 has a peripheral edge 38. The shaped dressing bolster 32 may be made of a number of different medical bolster materials, i.e., materials suitable for use in medical applications and that may be made sterile. In one illustrative embodiment, the shaped dressing bolster 32 is made from a medical bolster material that is a manifold material. The term "manifold" as used herein generally refers to a substance or structure that is provided to assist in applying reduced pressure to, delivering fluids to, or removing fluids from a tissue site. The manifold material typically includes a plurality of flow channels or pathways that distribute fluids provided to and removed from the tissue site around the manifold material. The flow channels or pathways may be interconnected. The manifold material may be a biocompatible material that is capable of being placed in contact with tissue site and distributing reduced pressure to the tissue site. Examples of manifold materials may include, for example, without limitation, materials that have structural elements arranged to form flow channels, such as, for example, cellular foam, open-cell foam, porous tissue collections, liquids, gels, and foams that include, or cure to include, flow channels.

The manifold material, or medical bolster material, may be porous and may be made from foam, gauze, felted mat, or any other material suited to a particular biological application. In one embodiment, the manifold material is a porous foam and includes a plurality of interconnected cells or pores that act as flow channels. The porous foam may be a polyurethane, open-cell, reticulated foam such as GranuFoam® material manufactured by Kinetic Concepts, Incorporated of San Antonio, Tex. Other embodiments may include "closed cells."

The reticulated pores of the Granufoam® material, that are typically in the range of about 400 to 600 microns, are helpful in carrying out the manifold function, but other materials may be used. The density of the medical bolster material, e.g., Granufoam® material, is typically in the range of about 1.3-1.6 lb/ft$^3$ (20.8 kg/m$^3$-25.6 kg/m$^3$). A material with a higher density (smaller pore size) than Granufoam® material may be desirable in some situations. For example, the Granufoam® material or similar material with a density greater than 1.6 lb/ft$^3$ (25.6 kg/m$^3$) may be used. As another example, the Granufoam® material or similar material with a density greater than 2.0 lb/ft$^3$ (32 kg/m$^3$) or 5.0 lb/ft$^3$ (80.1 kg/m$^3$) or even more may be used. The more dense the material is, the higher compressive force that may be generated for a given reduced pressure. If a foam with a density less than the tissue at the tissue site is used as the medical bolster material, a lifting force may be developed.

The medical bolster material may be a reticulated foam that is later felted to thickness of about ⅓ the foam's original thickness. Among the many possible materials, the following materials may be used: Granufoam® material or a Foamex® technical foam (www.foamex.com). In some instances it may be desirable to add ionic silver to the foam in a microbonding process or to add other substances to the medical bolster material such as antimicrobial agents. The medical bolster material may be isotropic or anisotropic depending on the exact orientation of the forces desired during reduced pressure. The medical bolster material could be a bio-absorbable material. A comfort layer of material may be added as well between the medical bolster material and the patient.

The sealing subsystem 60 includes an over-drape 62, or drape or sealing member. The over-drape 62 may be an elastomeric material or may be any material that provides a fluid seal. "Fluid seal," or "seal," means a seal adequate to hold reduced pressure at a desired site given the particular reduced-pressure subsystem involved. The over-drape 62 may, for example, be an impermeable or semi-permeable, elastomeric material. "Elastomeric" means having the properties of an elastomer. Elastomeric material is generally a polymeric material that has rubber-like properties. More specifically, most elastomers have elongation rates greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Specific examples of over-drape materials include a silicone drape, 3M Tegaderm® drape, acrylic drape such as one available from Avery Dennison, or an incise drape.

The over-drape 62 may be coupled to the shaped dressing bolster 32. If coupling is desired, the coupling may occur in many ways. The over-drape 62 and shaped dressing bolster 32 may be coupled using adhesives, such as an acrylic adhesive, silicone adhesive, hydrogel, hydrocolloid, etc. The over-drape 62 and shaped dressing bolster 32 may be bonded by using any technique, including without limitation welding (e.g., ultrasonic or RF welding), bonding, adhesives, cements, etc. The over-drape 62 and shaped dressing bolster 32 may be coupled partially, completely, or not at all. Structure may be added to the bond to make the over-drape 62 behave anisotropically in a desired direction, i.e. to make an anisotropic drape material. The anisotropic drape material is configured to move, contract, or expand in a given direction or axis to a greater extent compared to another direction or axis. This behavior is also discussed in connection with FIG. 9 below. As used herein, the term "coupled" includes coupling via a separate object and includes direct coupling. The term "coupled" also includes two or more components that are continuous with one another by virtue of each of the components being formed from the same piece of material. Also, the term "coupled" may include chemical, such as via a chemical bond, mechanical, thermal, or electrical coupling. Fluid coupling means that fluid is in communication between the designated parts or locations.

In the illustrative embodiment of FIG. 1, the over-drape 62 may be sized to extend beyond the shaped dressing bolster 32 to form a drape extension 64. The drape extension 64 has a first surface 66 and a second, tissue-facing surface 68. The over-drape 62 may be sealed against the epidermis 14 of the patient (or against another layer, such as a gasket or an additional sealing member) using a sealing apparatus 69 for providing a fluid seal. As used herein, reference to a seal on the patient's epidermis should be deemed to include sealing against another layer, such as a film gasket, which can contact and seal with the patient's epidermis. The fluid seal allows a reduced pressure to be maintained by the reduced-pressure subsystem 80. The sealing apparatus 69 may take numerous forms, such as an adhesive 70; a sealing tape, or drape tape or strip; double-side drape tape; paste; hydrocolloid; hydrogel; or other sealing means. If a tape is used, it may be formed of the same material as the over-drape 62 with a pre-applied, pressure-sensitive adhesive. The adhesive 70 may be applied on the second surface 68 of drape extension 64. The adhesive 70 provides a substantially fluid seal between the over-drape 62 and the epidermis 14 of the patient. Before the over-drape 62 is secured to the patient, adhesive 70 may have removable strips, or releasable backing, covering the adhesive 70. The over-drape 62 may be formed as an integral drape or formed by coupled segments or portions.

The reduced-pressure subsystem 80 includes a reduced-pressure source 82, or therapy unit. The reduced-pressure source 82 may be a vacuum pump, wall suction, or other source. The reduced-pressure source 82 provides reduced pressure as a part of the system 10. While the amount and nature of reduced pressure applied to a tissue site will typically vary according to the application, the reduced pressure will typically be between −5 mm Hg and −500 mm Hg and more typically between −100 mm Hg and −300 mm Hg.

In order to maximize patient mobility and ease, the reduced-pressure source 82 may be a battery-powered, single-use reduced-pressure generator. The battery-powered, single-use reduced-pressure generator facilitates application in the operating room and provides mobility and convenience for the patient during the rehabilitation phase. For many procedures, it is believed that the patient would be directed to wear the reduced-pressure system 10 for three to five days and may be directed to wear the reduced-pressure system 10 for 15 days or more. Still, this treatment time can be a time period less than conventional treatments, such as conventional compressive garments, which are often worn for up to six weeks. Accordingly, the battery life or power provisions for such a reduced-pressure source 82 may need to accommodate up to 15 days of operation. Other sources of reduced pressure may be utilized, such as V.A.C.® therapy unit, which is available from KCI of San Antonio, Tex., or a wall suction unit. The reduced-pressure source 82 could also be supplied by a portable mechanical device, such as a piston in a tube, depending on how much leakage there is with the fluid seal between the shaped dressing bolster 32 and the epidermis 14.

In the illustrative embodiment of FIG. 1, the reduced-pressure source 82 is shown having a battery compartment 84 and a canister region 86 with windows 88 that allow a visual indication of the level of fluid within canister 86. An interposed membrane filter, such as hydrophobic or oleophobic filter, may be interspersed between a reduced-pressure delivery conduit, or tubing, 90 and the reduced-pressure source 82.

The reduced pressure developed by reduced-pressure source 82 is delivered through the reduced-pressure delivery conduit 90 to a reduced-pressure interface 92, which may be an elbow port 94. In one illustrative embodiment, the elbow port 94 is a TRAC® technology port available from KCI of San Antonio, Tex. The reduced-pressure interface 92 allows the reduced pressure to be delivered through the sealing subsystem 60 and realized within an interior portion of sealing subsystem 60. In this illustrative embodiment, the port 94 extends through the over-drape 62 and into shaped dressing bolster 32.

In operation, the reduced-pressure system 10 may be applied in the operating room after a surgical procedure on the patient or applied elsewhere. The second surface 36 of the shaped dressing bolster 32, which may include a comfort layer (see, e.g., FIG. 16) would be placed against the patient's epidermis 14 with the shaped dressing bolster 32 placed over the damaged subcutaneous tissue site 20 and with a portion over the incision 12. The dressing assembly 30 may be pre-sized for the typical application involved in the procedure performed by a healthcare provider or sized at the time. The dressing assembly 30 may be sized, shaped, and configured to work in different anatomical applications such as abdominal, chest, thighs, extremities, etc.

If the over-drape 62 has not already been coupled (see other illustrative embodiments) to the shaped dressing bolster 32, the over-drape 62 would then be placed over the first surface 34 of the shaped dressing bolster 32 with an extra portion extending beyond the peripheral edge 38 to form the drape extensions 64. The drape extensions 64 may then be taped down (see 172 in FIG. 2) or an adhesive 70 (FIG. 1) used to form a fluid seal between the over-drape 62 and the patient's epidermis 14. The fluid seal need only be adequate to allow the reduced-pressure system 10 to hold a reduced pressure at a desired location. The reduced-pressure interface 92 would then be applied if not already installed, and the reduced-pressure delivery conduit 90 would be coupled at one end. The other end of the reduced-pressure delivery conduit 90 would then be coupled to the reduced-pressure source 82. The reduced-pressure source 82 may then be activated and a reduced pressure delivered to the shaped dressing bolster 32.

As the pressure is reduced at the shaped dressing bolster 32, the shaped dressing bolster 32 compresses and laterally contracts and forms a semi-rigid substrate, or a less-pliable substrate. The reduced pressure is transmitted through the shaped dressing bolster 32 so that the reduced pressure is applied to the patient's epidermis 14 at the point of the incision 12. At least at the early stages of the healing process and with certain types of wounds, the reduced pressure may be transmitted through the incision 12 and into the subcutaneous tissue 20 and the reduction of pressure may directly help close defects, such as the subcutaneous void 22, and generally provide stability to the area. The reduced pressure delivered to the shaped dressing bolster 32 also develops the compressive force 24 that again may provide stability, therapy, and may also close or help close the subcutaneous void 22. The compressive force 24 is preferably more than just at the epidermis 14. For example, the compressive force 24 can apply a force at the level of the subcutaneous tissue 20 or other subdermal anatomy.

As the over-drape 62 and shaped dressing bolster 32 laterally contract under the influence of the reduced pressure, and as the compressive force acts of the epidermis 14, the net closing force 26 develops that may help hold the incision 12 closed and may generally provide additional stability to the area. The effective tensile strength of the incision 12 may be increased. The closing force 26 may rely in part on friction between the shaped dressing bolster 32 and the epidermis 14 to communicate the closing force to the epidermis 14 and may involve force transmission from the drape extension 64 to the epidermis 14 by way of the adhesive 70 or through friction if tape (172 in FIG. 2) is used. At the same time, the reduced pressure delivered to and through shaped dressing bolster 32 helps to remove any exudates or other fluids from the incision 12. In one aspect, the reduced-pressure system 10 inhibits the formation of wrinkles in the epidermis 14. The system 10 can deliver an even amount of force to the epidermis 14 holding the epidermis 14 in a smooth, or non-wrinkled, configuration for healing.

Figure 2:
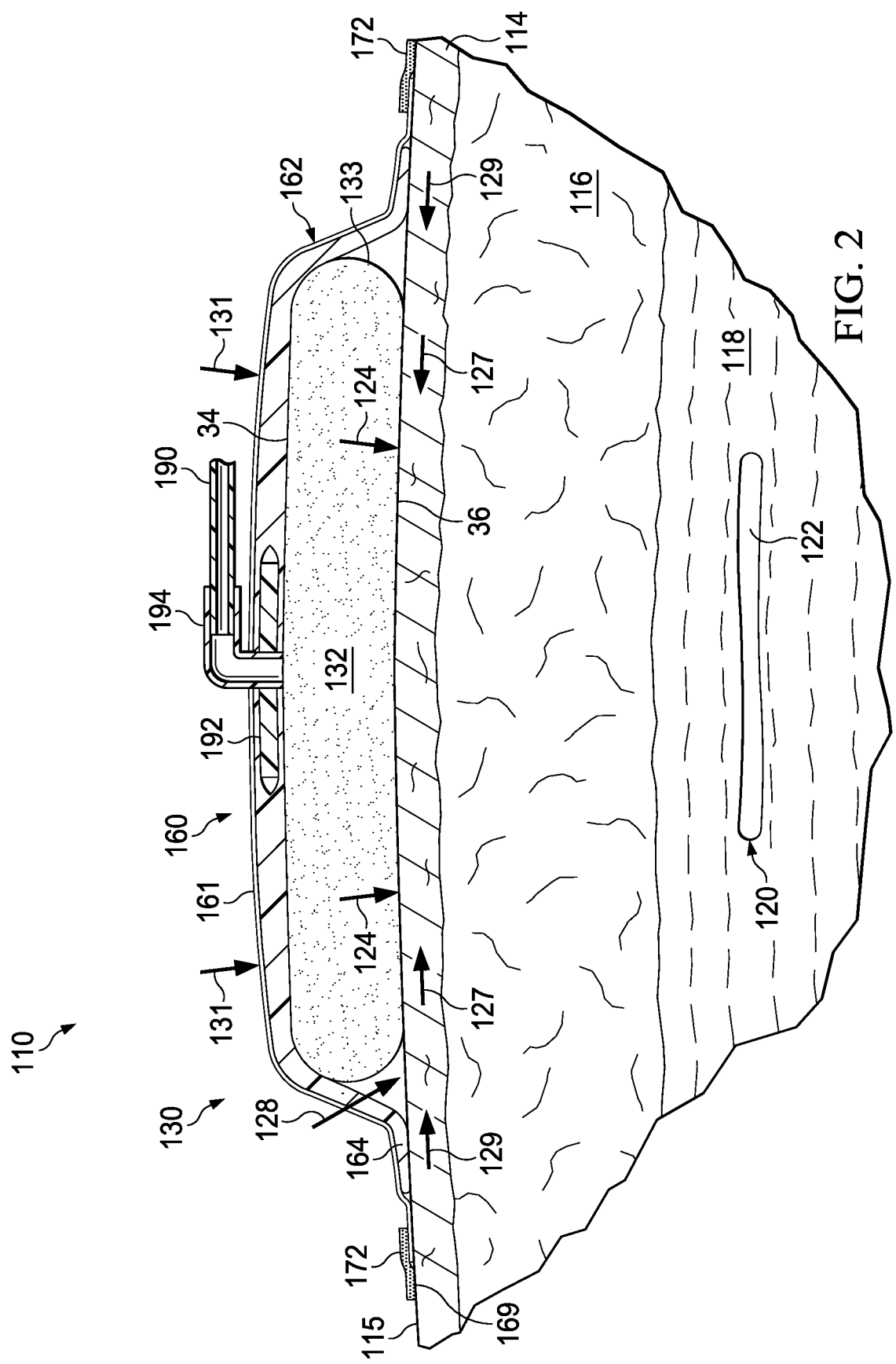
FIG. 2 is a schematic, cross-section of a portion of an illustrative embodiment of a reduced-pressure surgical wound treatment system shown on intact skin and over an area of damaged subcutaneous tissue.

The reduced-pressure system 10 may avoid skin irritation, such as blistering of the patient's epidermis 14, which may be due to secondary shear, secondary strain or other effects. To this end, the extremity 33 of the shaped dressing bolster 32 may be shaped to provide an even distribution of radial, compressive forces. The extremity 33 is the outer, shaped portion of the shaped dressing bolster 32 and the peripheral edge is generally the most outboard portion of the shaped dressing bolster 32 or the most outboard portion that interfaces with patient's skin. The extremity 33 may take a number of different shapes to help evenly distribute the compressive forces or otherwise avoid stress risers. The possible shapes for the extremity 33 include the following: a chamfered (or angled, beveled, or tapered) surface as shown in FIG. 1, an arcuate shape as shown in FIG. 2, or other shape that distributes the forces. In contrast, when a bolster with a square-edge is used, a "tent area" may form when an over-drape is applied over the bolster and onto the patient's epidermis. The "tent area" may contribute to skin irritation unless other steps are taken. The shaped dressing bolster 32 avoids the "tent area." The shaped edge, or extremity, of the dressing bolster allows a compressive force to be developed without a big "edge effect"; that is, without causing shear or stress to rise to a level that causes skin irritation, such as erythema or blistering. The shaped portion of the shaped dressing bolster 32 gradually distributes the force to avoid irritation. This way of carefully applying the forces to the skin to avoid irritation is generally referred to as "evenly distributing" the compressive force, but is not strictly used in a literal sense. As another precaution against skin irritation, an inner layer may be added between the shaped dressing bolster 32 and the patient's epidermis 14 (see, e.g., 857 in FIG. 11) or placed in other locations as explained in connection with other illustrative embodiments further below.

It may be desirable to apply the reduced-pressure system 10 in the operating room and allow the reduced-pressure system 10 to remain on the patient until adequate healing has taken place. In this regard, it may be desirable to form the over-drape 62, shaped dressing bolster 32, and any other layers from see-through materials to allow the healthcare provider to gain visual cues about the healing of the incision 12 and damaged subcutaneous tissue 20 without having to remove the dressing assembly 30.

Referring now to FIG. 2, another illustrative embodiment of a system 110 for treating damaged, or undermined or abnormal, subcutaneous tissue in a patient is presented. The system 110 is analogous in most respects to the reduced-pressure system 10 and a correlation of parts is generally indicated in this embodiment by indexing the numerals by 100 and may not be further referenced. In this particular illustrative embodiment, the system 110 is placed over intact epidermis tissue 115, i.e., there is no incision in this instance. There is, however, damaged subcutaneous tissue 120 including a subcutaneous void 122. The system 110 helps with damaged subcutaneous tissue 120 whether or not there is an incision.

While the shaped dressing bolster 32 of FIG. 1 was shown with a trapezoidal cross-section, the shaped dressing bolster 132 of FIG. 2 has a cross-section that is formed with a portion having radiused edges, or having an arcuate cross-section. The arcuate cross-section of the shaped dressing bolster 132 is an oval or elliptical shape. The shaped dressing bolster 132 may be shaped with a double-beveled cross-section or other shape. As before, the shape of the shaped dressing bolster 132 is to facilitate "evenly distributing" the radial, compressive force to an extent that skin irritation is avoided during use of the system 110. An extremity 133 of the shaped dressing bolster 132 is shown having an elliptical cross section. In the illustrative embodiment of FIG. 2, a sealing apparatus 169 provides a fluid seal between over-drape 162 and epidermis 114 of the patient, and, in this instance, is a sealing tape 172.

The developed forces will now be further described. Ambient pressure provides a vertical force 131 on a first surface 161 of the over-drape 162 and contraction of the shaped dressing bolster 132 develops a compressive force 124 to provide a force that is directed toward the epidermis 114 and that reaches to the subcutaneous levels, i.e., to subcutaneous tissue 118. At the same time, a lateral force, or closing force, can be developed. The closing force is transferred to the epidermis through the shaped dressing bolster 132. A force 127 is an inward contraction force caused by the shaped dressing bolster 132 contracting and compressing. As the shaped dressing bolster 132 contracts and compresses, the closing force is transferred to the epidermis 114 through the shaped dressing bolster 132. At the same time, for this illustrative embodiment, as the reduced pressure is applied, the over-drape 162 is drawn into the area proximate the extremity 133 as suggested by arrow 128. Because a drape extension 164 is secured to the epidermis 114, the horizontal component of force 128 would pull the epidermis inward as is suggested by the inward closing force 129.

Figure 3:
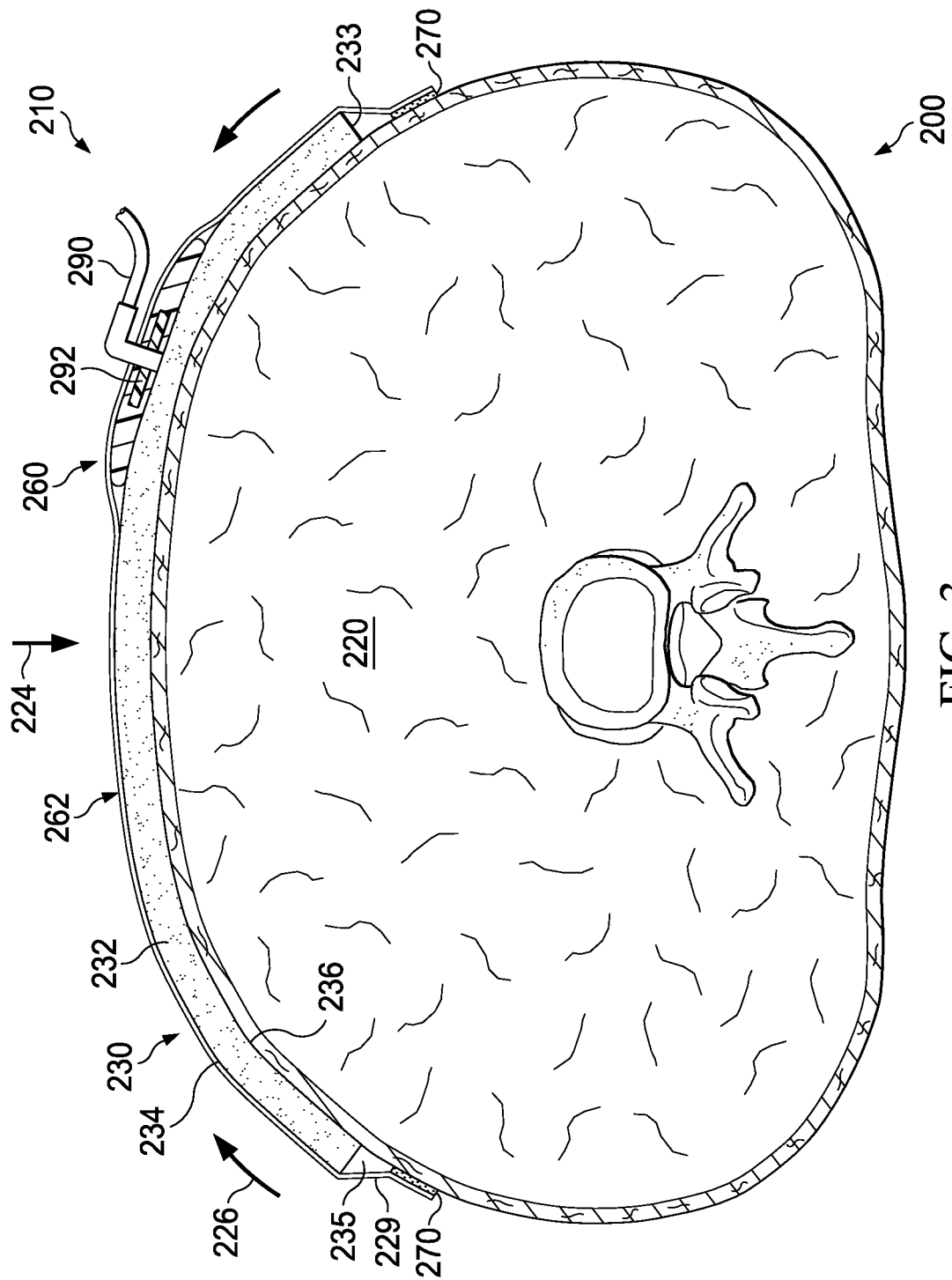
FIG. 3 is a schematic, cross-section of a portion of an illustrative embodiment of a reduced-pressure surgical wound treatment system shown deployed on a torso of a patient.

Referring now primarily to FIG. 3, a system 210 for treating tissue, such as damaged subcutaneous tissue 220, is shown on a curved body part 200 such as a patient's torso. A dressing assembly 230 includes a shaped dressing bolster 232. A sealing subsystem 260 includes an over-drape 262 and an attachment device 270. A reduced-pressure source (not shown) provides reduced pressure to a reduced-pressure delivery conduit 290, which delivers the reduced pressure to a reduced-pressure interface 292, which in turn delivers the reduced pressure to the shaped dressing bolster 232. As the shaped dressing bolster 232 is compressed under the influence of a reduced pressure, a net radial, compressive force 224 is developed that is delivered to the subcutaneous tissue 220. The over-drape 262 forms a "tent" area around a void 235. Under reduced pressure, the over-drape 262 is pulled into the void 235 and a force is thereby applied that develops an inward contracting force 226. Alternatively, an extremity of the shaped dressing bolster 232 may be shaped to avoid the tent area or the over-drape may be attached to the extremity of the shaped dressing bolster 232.

In the embodiment of FIG. 3, the curvature of the shaped dressing bolster 232 also helps develop the compressive force. A first surface 234 of shaped dressing bolster 232 has a greater surface area than a surface area of a second, inward-facing surface 236 of the shaped dressing bolster 232, and under reduced pressure this difference in surface area also facilitates the development of the net compressive force 224.

Figure 4:
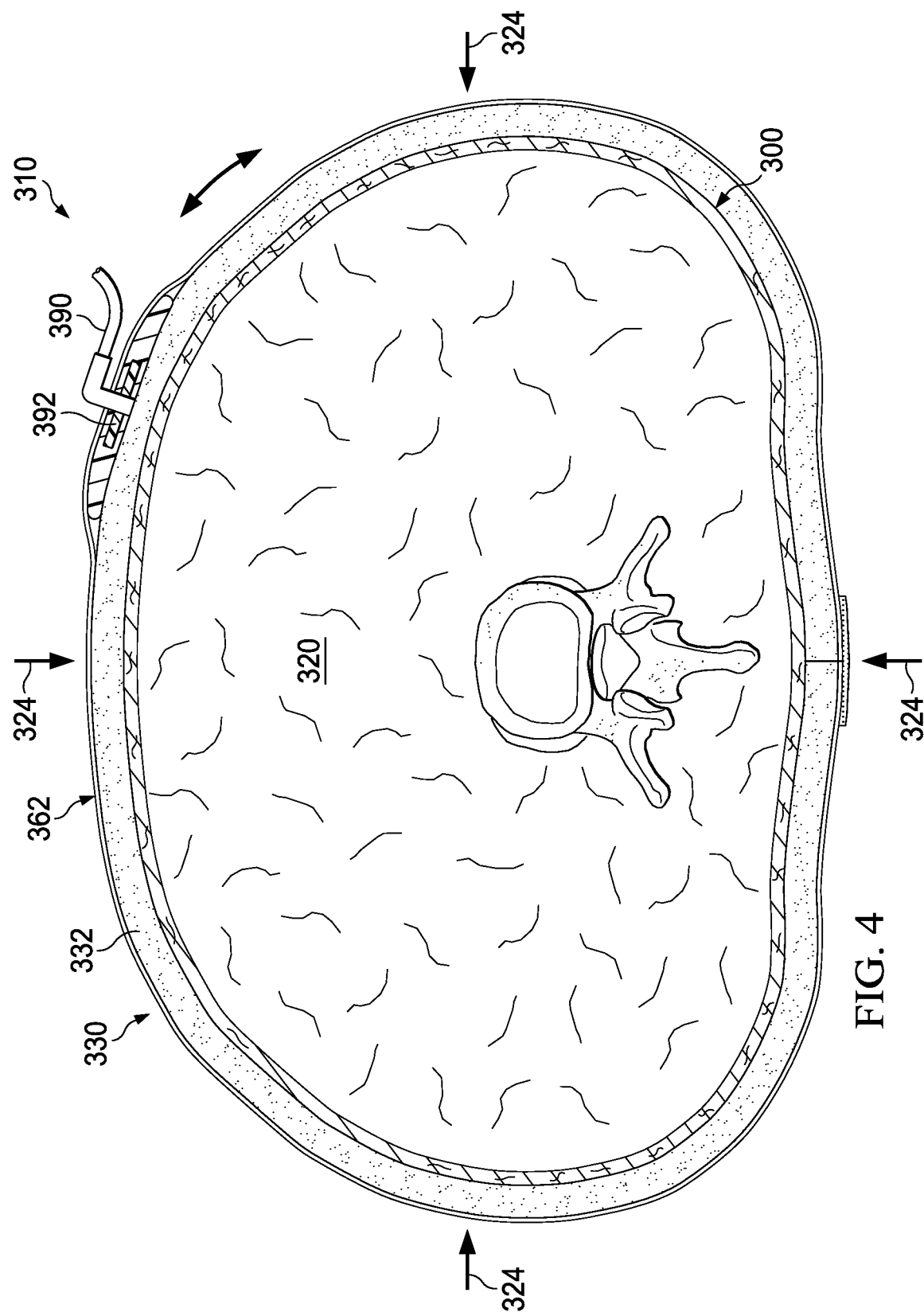
FIG. 4 is a schematic, cross-section of a portion of an illustrative embodiment of a reduced-pressure surgical wound treatment system shown deployed on a torso of a patient.

Referring now primarily to FIG. 4, an illustrative system 310 is presented. The system 310 is generally analogous in most respects to that of the system 210 of FIG. 3 and analogous parts are indicated by indexing the reference numerals of FIG. 3 by 100 and may not be further mentioned. The system 310 shows a circumferential dressing assembly 330, which in this illustrative embodiment completely extends around a circumference of a torso. Circumferential forces are developed during the application of reduced pressure and combine in the system 310 to develop the net radial, compressive force 324. The compressive force 324 can be relatively higher than a flat or partial-torso application because there is no off-loading of force to the drape and to the epidermis.

Figure 5:
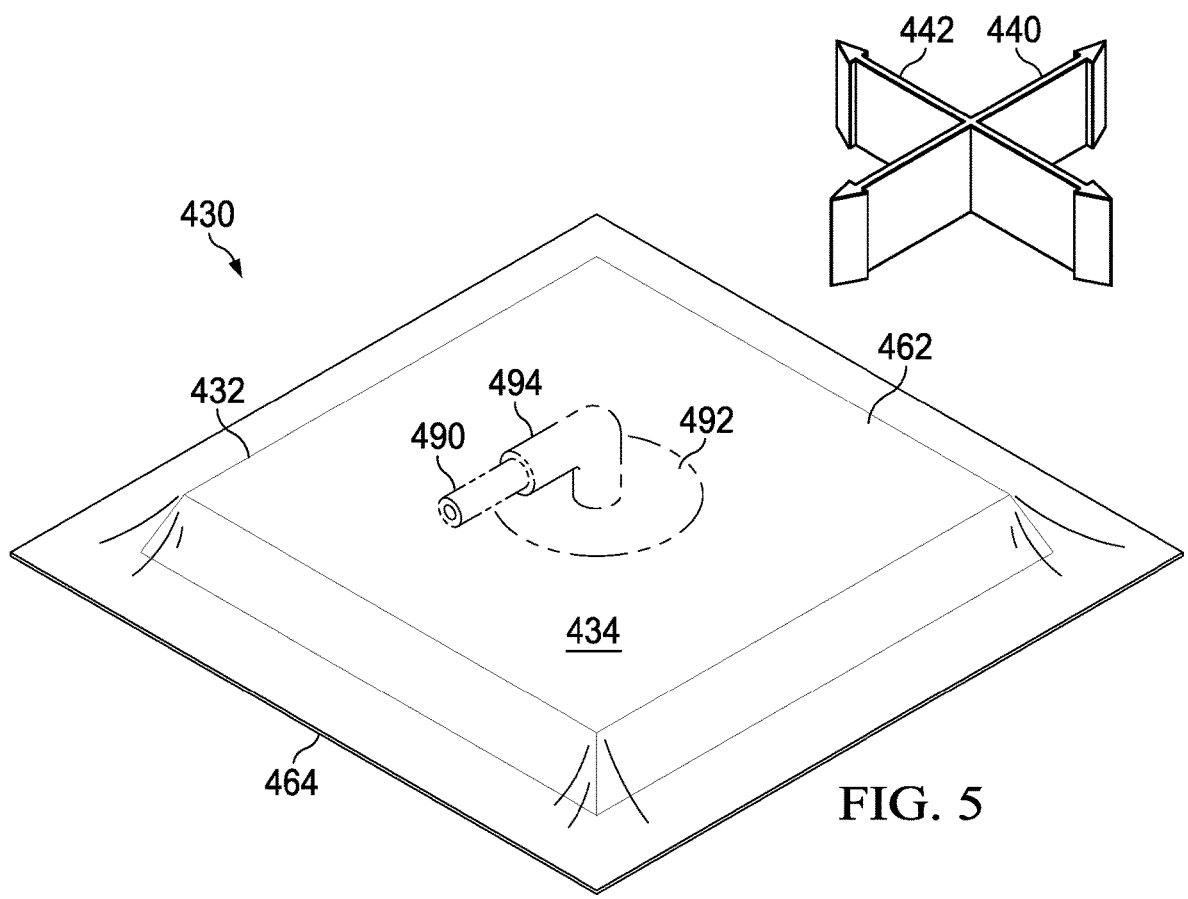
FIG. 5 is a schematic, perspective view of an illustrative embodiment of a dressing assembly.
Figure 6:
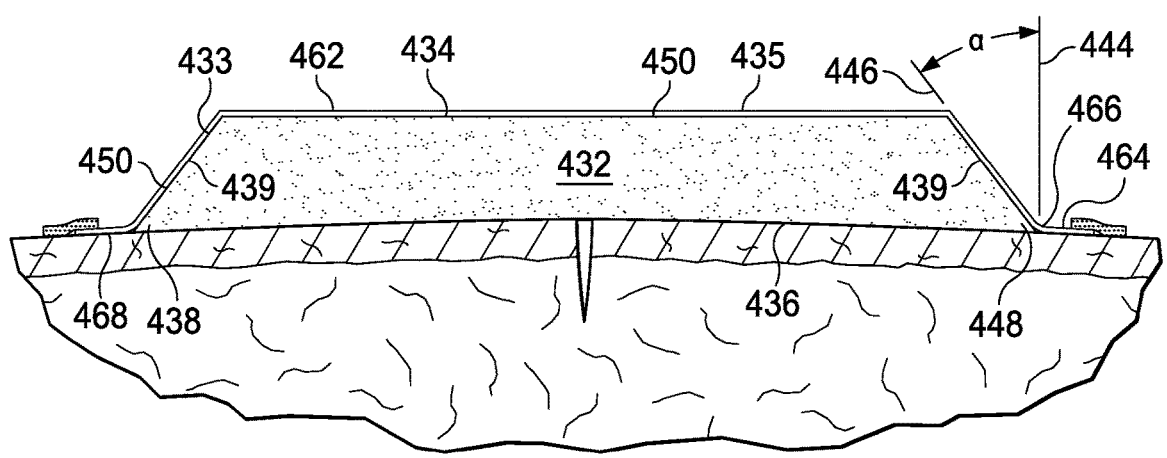
FIG. 6 is a schematic, cross-section of the illustrative embodiment of the dressing assembly of FIG. 5.

Referring now primarily to FIGS. 5 and 6, another illustrative embodiment of a dressing assembly 430 is presented. The dressing assembly 430 has a shaped dressing bolster 432 with a first surface 434 and a second, inward-facing (skin-facing or patient-facing) surface 436. In this illustrative embodiment, the shaped dressing bolster 432 has been formed with an oblique extremity 433, and in particular with a trapezoidal cross-section in two orthogonal planes, such as orthogonal planes 440 and 442. A cross-section along one such plane of the dressing assembly 430 is shown in FIG. 6. The peripheral edge 438 of the shaped dressing bolster 432 is formed with an angle alpha (α) between a vertical (for the orientation shown), or normal, reference line 444 and a surface extension line (in cross-section) 446. The angle alpha (α) would typically be between 3 degrees and 95 degrees, and more typically between 20 and 65 degrees, and more typically still about 45 degrees.

An over-drape 462 is placed over the shaped dressing bolster 432. The over-drape 462 extends beyond a peripheral edge 438 to form drape extensions 464, each having a first side 466 and a second, inward-facing surface 468. The over-drape 462 may be coupled using any of a number of devices or techniques, such as with adhesives and bonding as previously mentioned. In this illustrative embodiment, the over-drape 462 is coupled by a bond 450 to an exterior 439 of the peripheral edge 438. The over-drape 462 may also be coupled to an exterior surface 435 of the first surface 434 of the shaped dressing bolster 432. In this illustrative embodiment, the over-drape 462 may be coupled, at least partially, to substantially all of the exterior surfaces of the shaped dressing bolster 432, except the surface facing the patient. When the over-drape 462 is coupled to substantially all the exterior surfaces of the shaped dressing bolster 432 except the inward-facing surface, the peripheral edge 438 may be shaped to have right angles and yet avoid skin irritation because no "tent area" can form. Otherwise, the edge 438 is shaped to be other than at a right angle. Alternatively, a layer may be added to help minimize skin irritation.

As shown in FIG. 5, a reduced-pressure delivery conduit 490, which is part of a reduced-pressure subsystem, can be used to supply reduced pressure to a reduced-pressure interface 492 that delivers reduced pressure into the shaped dressing bolster 432. The reduced-pressure interface 492 may be a port 494 or a direct application into the bolster 432 or other device.

Figure 7:
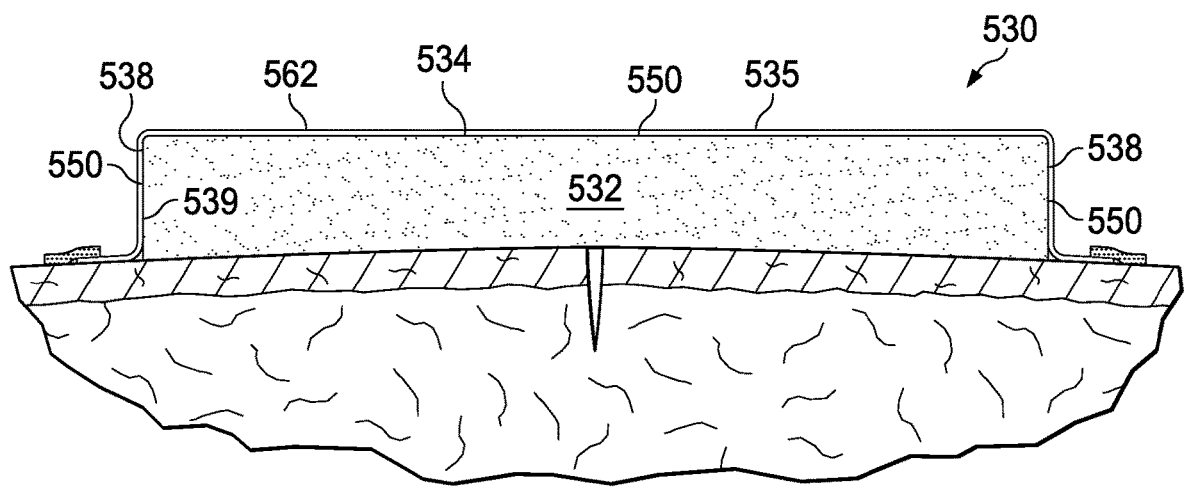
FIG. 7 is a schematic, cross-section of an illustrative embodiment of another dressing assembly.

Referring now primarily to FIG. 7, another illustrative embodiment of a dressing assembly 530 is presented. The dressing assembly 530 has a shaped dressing bolster 532 formed to have a rectangular cross-section. In this instance, an over-drape 562 is coupled, such as by bonding with bond 550, to an exterior surface 539 of a peripheral edge 538 and to a first surface 534 of the shaped dressing bolster 532. The bond 550 may facilitate more even application of the radial, compressive force to the patient even though the shaped dressing bolster 532 is shaped with right angles. While the coupling is shown as complete along the exterior 539 of the peripheral edge 538 and on an exterior surface 535 of the first surface 534, the coupled portion may be partial or accomplished with tacking.

Figure 8:
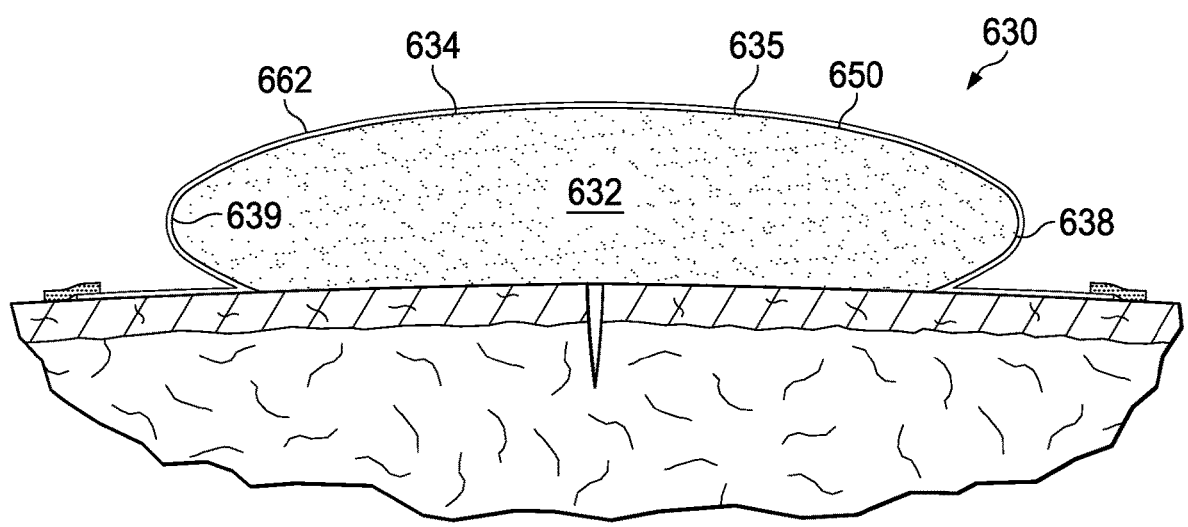
FIG. 8 is a schematic, cross-section of an illustrative embodiment of another dressing assembly.

Referring now primarily to FIG. 8, another illustrative embodiment of a dressing assembly 630 is presented. The dressing assembly 630 has a shaped dressing bolster 632 that is formed to have an arcuate cross-section, which, in this instance, is an elliptical or oval cross-section. As such, the peripheral edge 638 has a radius or curved shape. The over-drape 662 may be coupled by bonding 650 on an exterior surface 639 of the peripheral edge 638 and on an exterior surface 635 of a first surface 634 of the shaped dressing bolster 632. The elliptical cross-section may exist in two different orthogonal planes.

Figure 9:
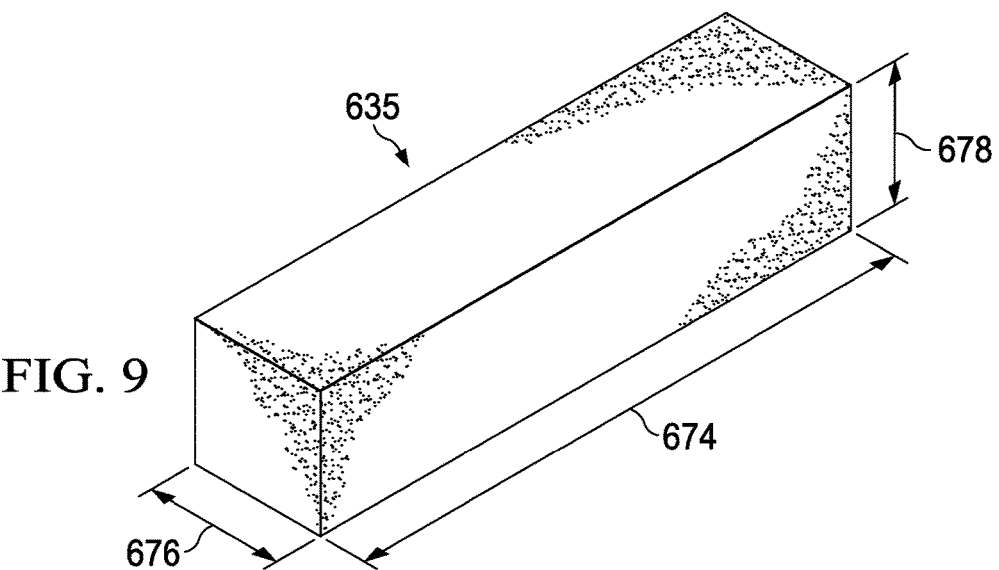
FIG. 9 is a schematic, perspective view of a portion of an illustrative embodiment of a dressing assembly.

Referring now primarily to FIG. 9, an illustrative embodiment of a medical bolster material 635 is presented with reference to a first axis 674, a second axis 676, and a third axis 678. The medical bolster material 635 may be used for any of the shaped dressing bolsters previously mentioned. While in many applications, the medical bolster material 635 may be isotropic, in other applications it may be desirable to have an anisotropic material like the medical bolster material 635.

Anisotrophy is generally the property of being directionally dependent, as opposed to isotropy, which means homogeneity in all directions. For example, if it is desirable to produce a stronger force that opposes gravity that is applied to an exterior of a patient, anisotropic material may be used so that when net circumferential force is developed along the first axis 674, a greater movement is developed along the vertical axis—in this instance the third axis 678 for the orientation shown. In still other instances, it may be desirable to also have a different performance in the direction of the second axis 676. The anisotropic material may be formed by adding filaments in a first direction. The anisotropic material may also be formed by felting (heat compression) of the material to make lines of differing densities. The anisotropic material may also be formed by using an adhesive that imparts strength in a given direction.

Figure 10:
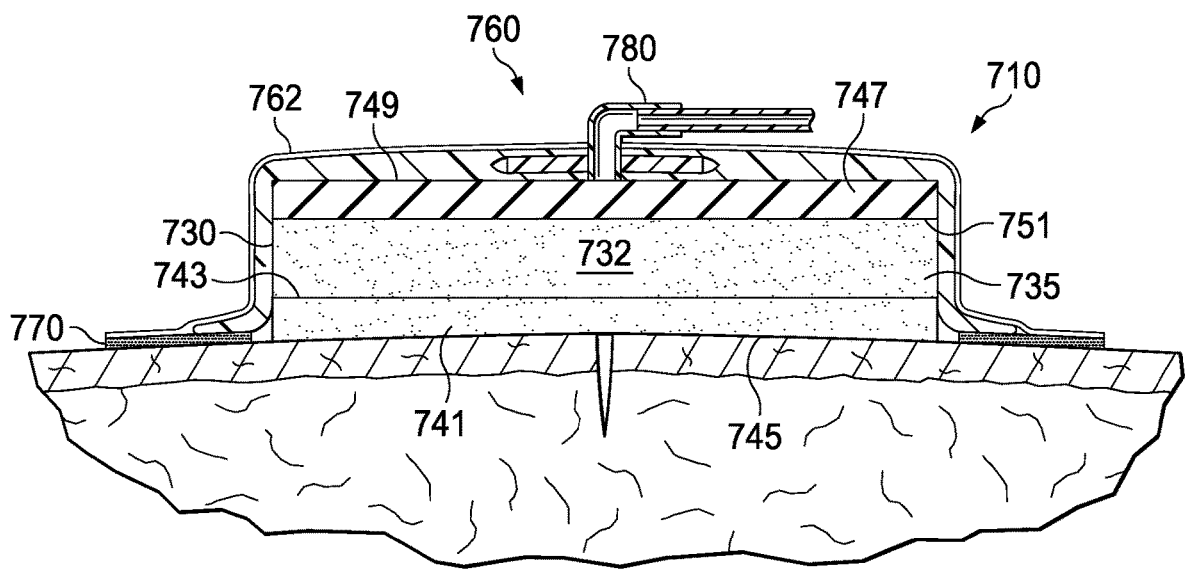
FIG. 10 is a schematic, cross-section of an illustrative embodiment of a dressing assembly.

Referring now primarily to FIG. 10, a portion of an illustrative embodiment of a system 710 for treating tissue, such as damaged subcutaneous tissue, is shown. The system 710 includes a shaped dressing bolster 735, a sealing subsystem 760, and a reduced-pressure subsystem 780 for which only a portion is shown. The shaped dressing bolster 735 may be part of a dressing assembly 730 that includes a breathable dry layer 741 having a first surface 743 and a second, inward-facing surface 745. The dressing assembly 730 also may include a non-breathable layer 747, which has a first surface 749 and a second, inward-facing surface 751. The sealing subsystem 760 includes an over-drape 762 similar to the previously discussed embodiments and an attachment device 770.

A number of materials are possible for the various layers 741, 732, 747. The breathable dry layer 741 may be formed, for example, from a hydrophilic non-woven material that allows fluids to flow into the shaped dressing bolster 735. The breathable dry layer 741 may be a comfort layer that helps avoid skin irritation or otherwise enhances comfort. The shaped dressing bolster 735 may be formed from a relatively thin absorbent structure or material that can store relatively large quantities of fluid. For example, the shaped dressing bolster 735 may be formed from a superabsorbent polymer (SAP) of the type often referred to as "hydrogels," "super-absorbents," or "hydrocolloids." The shaped dressing bolster 735 may also be formed from any of the previously mentioned manifold materials. The non-breathable layer 747 may be formed from a number of different materials, e.g., a polyethylene film that will keep fluids from leaking out. Additional substrates may be added. The various layers 741, 732, 747 may be sealed or combined with adhesives such as a hot melt adhesive or heat bonded or coupled using any technique or device.

In operation, as fluid is added to the shaped dressing bolster 735, the shaped dressing bolster 735 becomes more rigid (less pliable), and under reduced pressure, this results in an increased radial, compressive force, such as radial force 24 in FIG. 1. The fluid may come in the form of exudates or other fluids from the wound or may be a supplied fluid such as a saline that is intentionally added through a second port, second lumen, or by injecting through the dressing assembly in an injection port. In this sense, the shaped dressing bolster 735 may be regarded as a liquid-controlled bolster since additional liquid can be added to make the shaped dressing bolster 735 more rigid (less pliable) and that results in a greater force.

Still referring to FIG. 10, an alternative illustrative embodiment of the dressing assembly 730 is presented by describing other possible elements. In this illustrative embodiment, the bolster includes two members: a first bolster layer 741, which is formed from a hydrophilic foam, and a second bolster layer 732, which is formed from a hydrophobic foam. The over-drape 762 is then placed over a first surface (top surface for orientation shown) of the second bolster layer 732. Other layers of various materials may be added as well.

Figure 11:
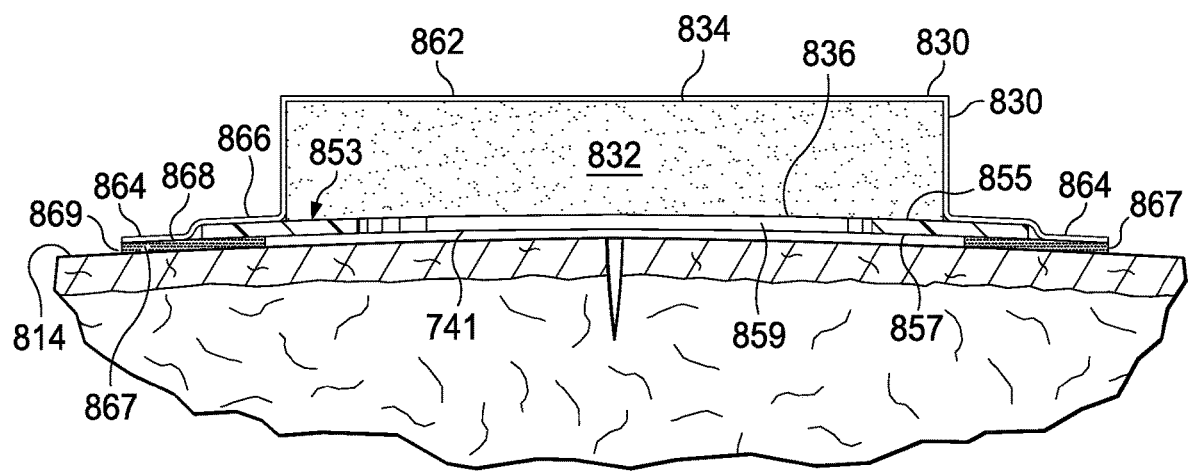
FIG. 11 is a schematic, cross-section of an illustrative embodiment of a dressing assembly.

Referring now primarily to FIG. 11, an illustrative embodiment of a dressing assembly 830 for use with a system for treating tissue, e.g., damaged subcutaneous tissue, is presented. The dressing assembly 830 includes a shaped dressing bolster 832 and an over-drape 862, which are generally analogous to those presented in other embodiments herein. A sealing subsystem 830 includes the over-drape 862 that extends beyond the shaped dressing bolster 832 to form drape extensions 864, which have a first surface 866 and a second, inward-facing side, 868. A sealing apparatus 869 may be used to provide a seal between the drape extension 864 and the patient's epidermis 814. In this illustrative embodiment, the sealing apparatus 869 is an adhesive 867, which is placed on the surface facing the patient. The adhesive 867 may initially be covered with a covering, or releasable backing, that may be peeled off before the dressing assembly 830 is applied to a patient's epidermis 814. The dressing assembly 830 shows the addition of an inner layer 853 having a first surface 855 and a second, inward-facing surface 857. The inner layer 853 is formed with a treatment-area aperture 859.

The inner layer 853 may help reduce or eliminate skin irritation that may result between the shaped dressing bolster 832 and the patient's epidermis 814. The inner layer 853 may be an acrylic drape material such as an Avery® brand Acrylic drape, a Scapa brand Silicone drape, or another suitable material. The inner layer 853 is placed around a perimeter of the second surface 836 of the shaped dressing bolster 832 where the shaped dressing bolster 832 would otherwise interface's with the patient's skin. The inner layer 853 and the over-drape 862 encapsulate the shaped dressing bolster 832, except for the treatment area aperture 859. An adhesive may be applied on the second surface 857 of the inner layer 853 to promote a splinting effect over an area where the shaped dressing bolster's 832 interaction with the epidermis ends and the over-drape's 862 interaction with the epidermis begins. This arrangement may help to prevent blistering due to high concentrations of shear stress and strain when the reduced pressure is applied because the adhesive is believed to help deter the epidermis from rolling or balling up and forming a pressure point or pressure rise.

Figure 12:
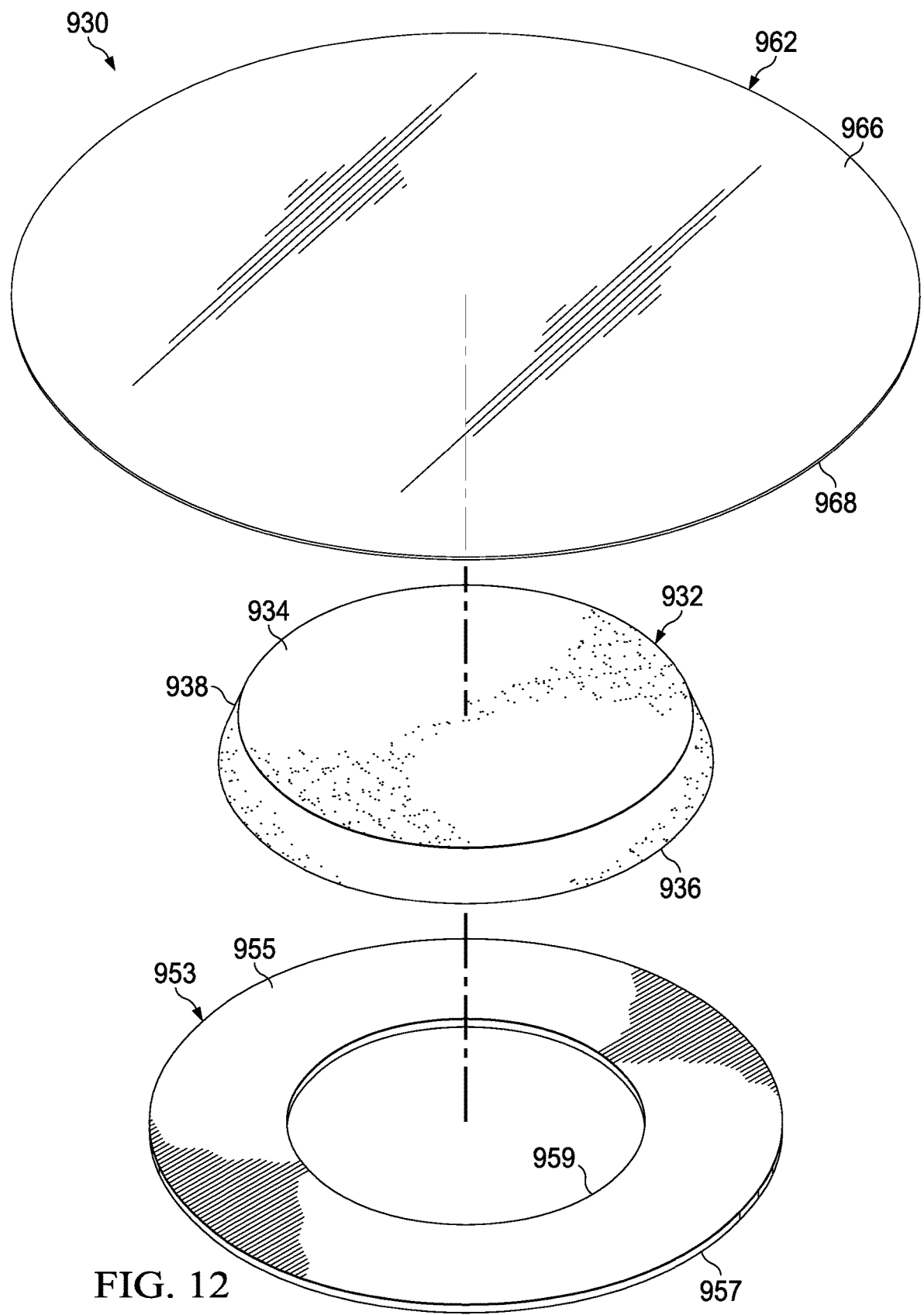
FIG. 12 is an exploded, schematic, perspective view of an illustrative embodiment of a dressing assembly.

Referring now primarily to FIG. 12, an illustrative embodiment of a dressing assembly 930 is shown in an exploded view. The dressing assembly 930 has a shaped dressing bolster 932, an inner layer 953, and an over-drape 962. The inner layer 953 has a first surface 955, a second, inward-facing surface 957, and is formed with a treatment-area aperture 959. The shaped dressing bolster 932 is an example of a shaped dressing bolster 932 having an oblique surface (peripheral edge 938 is formed with angle to a vertical axis) and thus, in this instance, forms a trapezoidal cross-section in at least two orthogonal planes. The shaped dressing bolster 932 has a first surface 934 and a second, inward-facing surface 936. The over-drape 962 has a first surface 966 and a second, inward-facing surface 968.

The inner layer 953 may be used in a number of ways to address the potential for skin irritation. In one illustrative embodiment, the second surface 936 of the shaped dressing bolster 932 is coupled to the first surface 955 of the inner layer 953. In another illustrative embodiment, no adhesive or other attachment device is used between the shaped dressing bolster 932 and the inner layer 953 so as to allow relative movement between the shaped dressing bolster 932 and the inner layer 953. Similarly, the second surface 968 of the over-drape 962 may be coupled to the first surface 934 of the shaped dressing bolster 932. In an alternative embodiment, there may be no attachment device between surfaces 934 and 968.

Still another illustrative embodiment involves coupling all the exterior surfaces of the shaped dressing bolster 932 to the over-drape 962, except the second, inward-facing surface 936 of the shaped dressing bolster 932. An adhesive or other attachment device may be used to couple the first surface 955 of the inner layer 953 to the second surface 936 of the shaped dressing bolster 932. No adhesive or attachment device is administered on the second surface 957 and so skin irritation may be reduced because the relatively low friction surface of the inner layer 953 is allowed to slide relative to the skin. Alternatively, an adhesive or other attachment device may be applied on the second surface 957 of the inner layer 953 to hold the inner layer 953 to the epidermis, but not between the shaped dressing bolster 932 and the inner layer 953 so as to allow lower-friction movement between the shaped dressing bolster 932 and the inner layer 953.

In yet another alternative of this illustrative embodiment, an adhesive or other adhesive device may be applied between the second surface 936 of the shaped dressing bolster 932 and the first surface 955 of the inner layer 953 and between the second surface 957 of the inner 953 and the patient's epidermis. With this alternative, a splinting effect is achieved in the area where the interaction of the shaped dressing bolster 932 with the epidermis ends and the inner layer's 953 interaction with the epidermis begins. This arrangement helps to prevent blistering due to high concentrations of shear stress and strain placed in that location when reduced pressure is applied. The adhesive or attachment device is believed to prevent the epidermis from rolling or balling up and forming a pressure point or pressure rise. The inner layer 953 configurations may be used on any of the illustrative embodiments presented as well as others.

Figure 13:
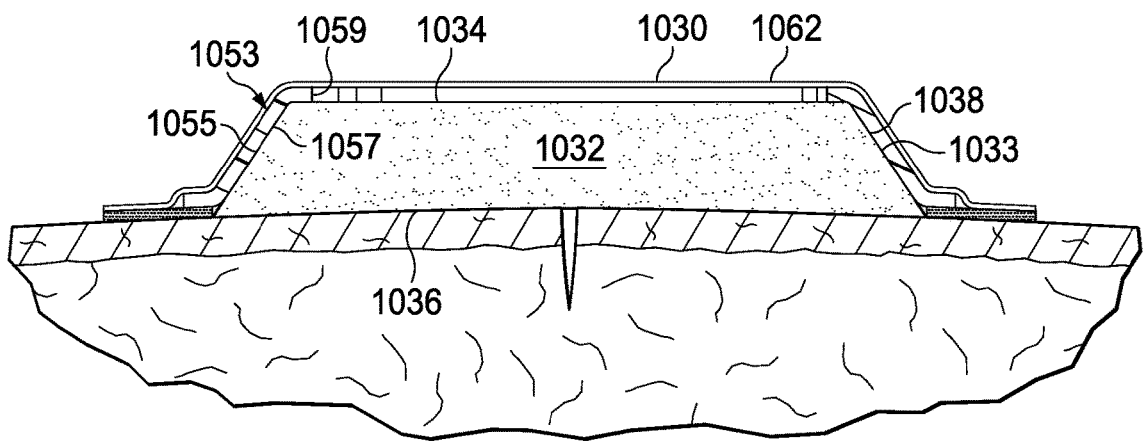
FIG. 13 is a schematic, cross-section of an illustrative embodiment of a dressing assembly.
Figure 14:
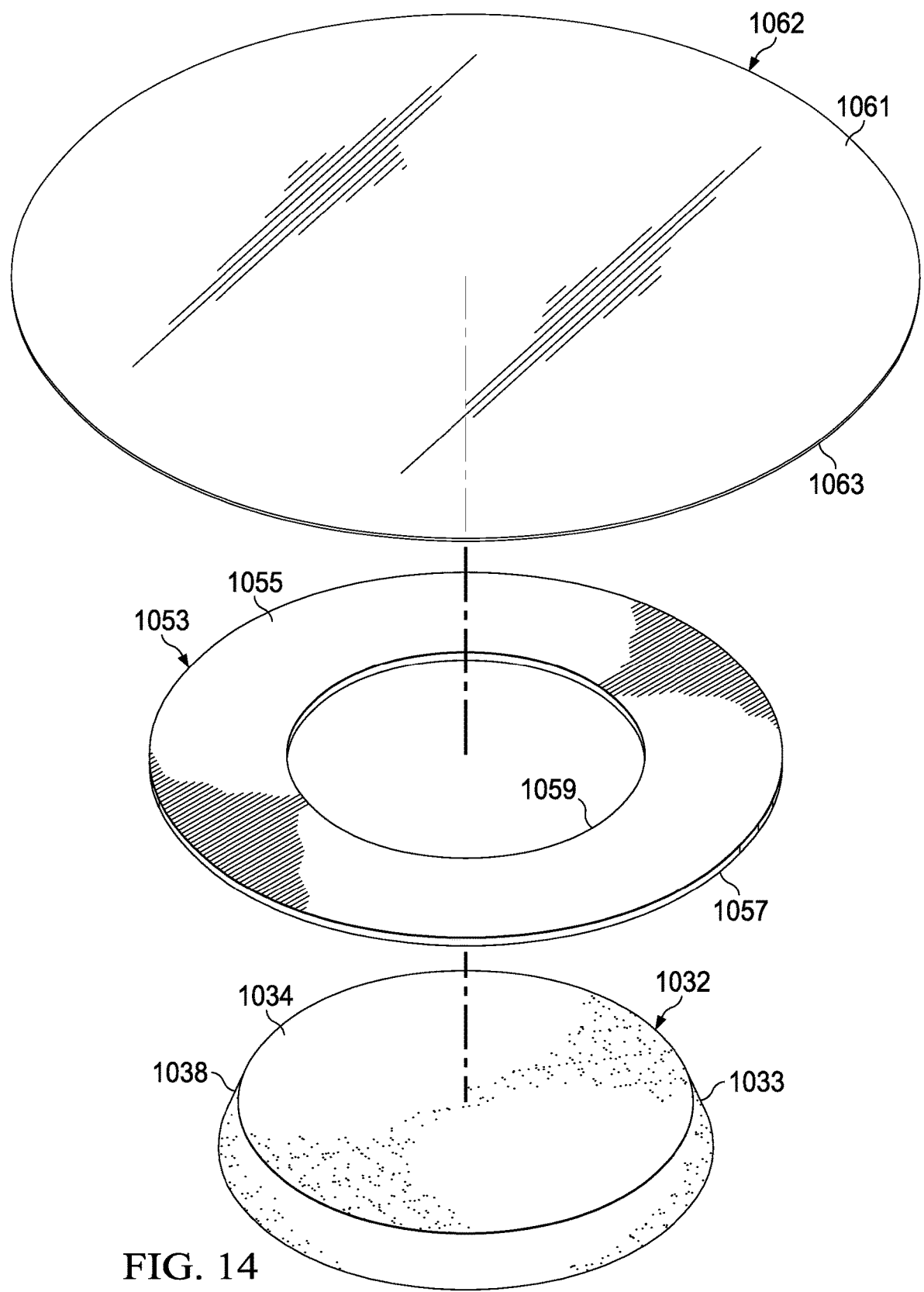
FIG. 14 is an exploded, schematic, perspective view of an illustrative embodiment of a dressing assembly.

Referring now primarily to FIGS. 13 and 14, an illustrative embodiment of a dressing assembly 1030 is presented. The dressing assembly 1030 has a shaped dressing bolster 1032 with a first surface 1034 and a second surface 1036. An extremity 1033 of the shaped dressing bolster 1032 is angled in this illustrative embodiment. An inner layer 1053 is provided having a first surface 1055 and a second, inward-facing surface 1057, but in this instance, the second surface 1057 is placed adjacent to the peripheral edge 1038 of the shaped dressing bolster 1032. The inner layer 1053 is formed with a central aperture 1059. The inner layer 1053 and a portion of shaped dressing bolster 1032 are covered with an over-drape 1062. Adhesive or another attachment device may be used between the first surface 1055 of the inner layer 1053 and second surface 1063 of the over-drape 1061 or between the second surface 1057 of the inner drape 1053 and the first surface 1034 of the shaped dressing bolster 1032.

Figure 15:
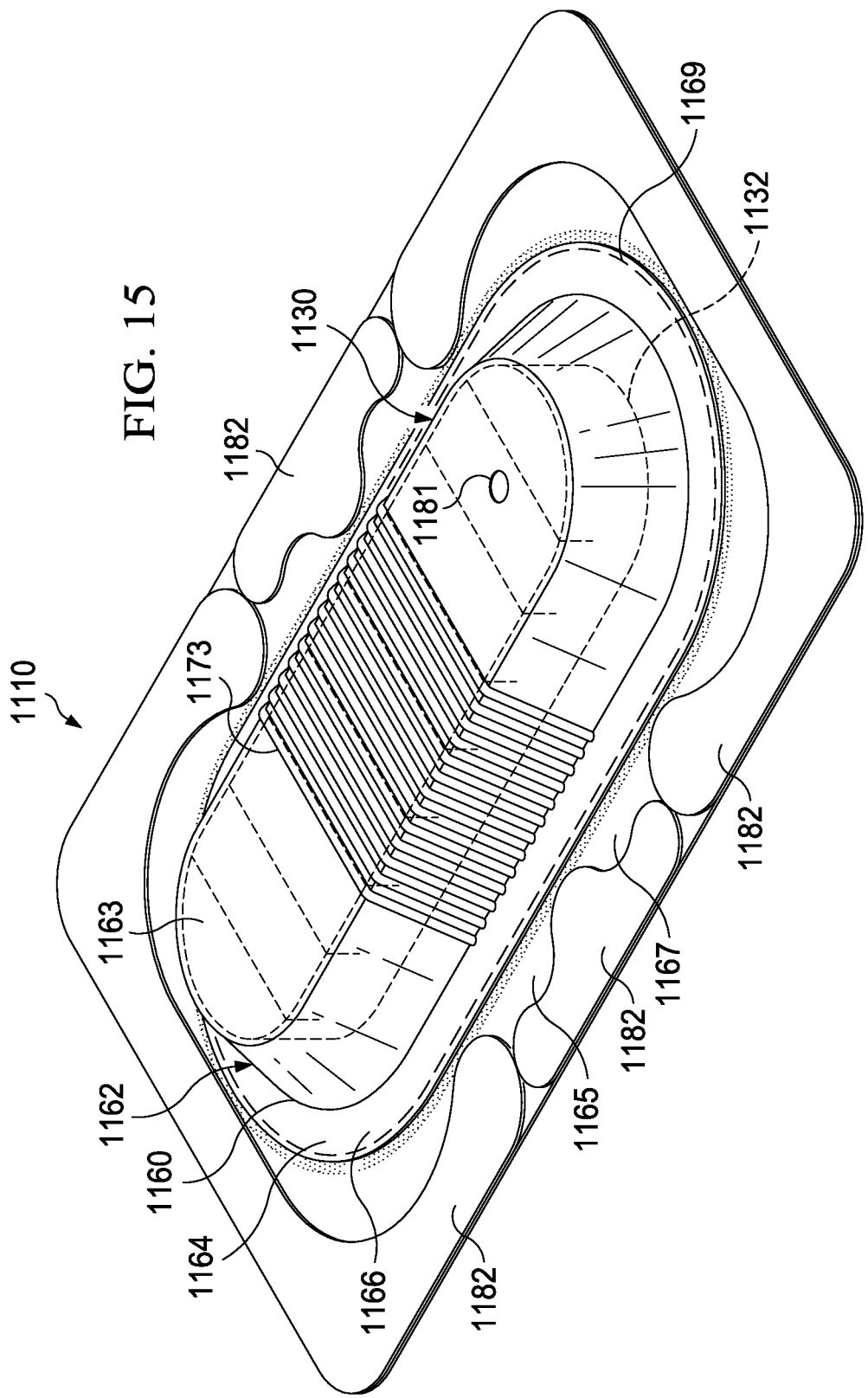
FIG. 15 is a schematic, perspective view of an illustrative embodiment of a dressing assembly.
Figure 16:
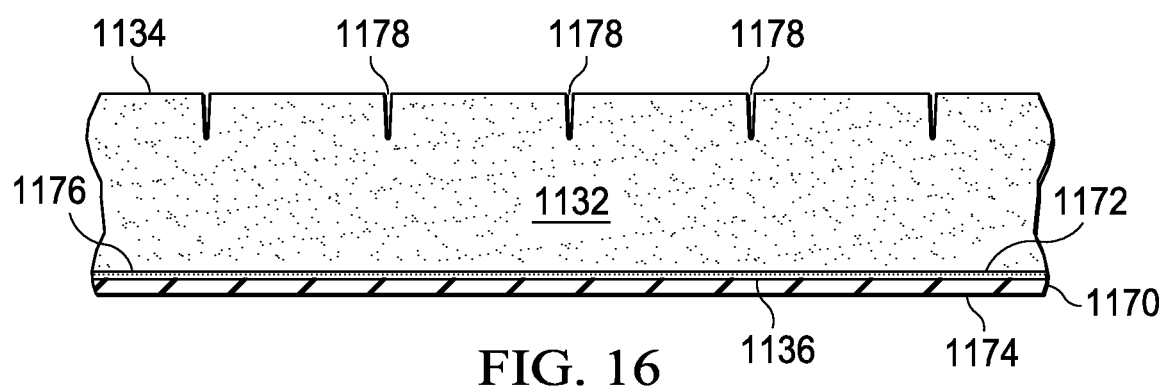
FIG. 16 is a cross sectional view of a portion of the dressing assembly of FIG. 15.

Referring now primarily to FIGS. 15-16, a portion of a system 1110 for treating a linear wound, area wound, other wound, or graft is presented. The portion of the system 1110 is presented in FIG. 15 in a pre-deployment state.

The system 1110 includes a dressing assembly 1130, which includes a shaped dressing bolster 1132. The shaped dressing bolster 1132 has a first side 1134 and a second, inward-facing side 1136. The shaped dressing bolster 1132 may be formed from any medical bolster material as previously discussed with other embodiments. A comfort layer 1170, which has a first side 1172 and a second, inward-facing side 1174, may be coupled, e.g., by a heat bond 1176 or any other technique, to the second side 1136 of the shaped dressing bolster 1132.

The comfort layer 1170 may be any material that helps prevent skin irritation and discomfort while allowing fluid transmission through the comfort layer 1170. As one non-limiting example, a woven, elastic material may be used or a polyester knit textile substrate. As another non-limiting example, an InterDry™ textile material from Milliken Chemical of Spartanburg, S.C., may be used. The comfort layer 1170 may include anti-microbial substances, such as silver. The comfort layer may be made like the breathable, dry layer 741 of FIG. 10.

In one embodiment, the shaped dressing bolster 1132 may include a plurality of flexibility notches 1178. The flexibility notches 1178 may be lateral notches, or lateral cuts, in the shaped dressing bolster 1132 as shown and, in addition or alternatively, may be one or more longitudinal notches, or longitudinal cuts, or other cuts. The cuts may be made using a saw (or notched blade), a hot knife, or other device. The flexibility notches 1178 enhance flexibility of the shaped dressing bolster 1132. The enhanced flexibility may be particularly useful when the dressing assembly 1130 is applied over a patient's joint or other area of movement. For example, if the shaped dressing bolster 1132 is used on a knee, the shaped dressing bolster 1132 may need to flex or extend as much as 100% or more, and the flexibility notches 1178 or ridges help provide the desired flexibility. In addition, a plurality of folds 1173 may be added to facilitate movement as described further below.

In one illustrative embodiment, the shaped dressing bolster 1132 is manufactured as follows. A block of Granufoam® material, e.g., 1.21 meter×1.8 meter×0.5 meter block, is cut to have a 19 mm height, and a saw is used to form lateral grooves, or lateral flexibility notches 1178. Then, a dry layer, which may be the comfort layer 1170, is laminated onto the second, or bottom, surface. Then, the foam block is cut using a die cut to form the individual shaped dressing bolsters 1132.

A sealing subsystem 1160 provides a fluid seal over the dressing assembly 1130 and at least a portion of the patient's epidermis. The sealing subsystem 1160 includes an over-drape 1162, which may be formed with a first over-drape portion 1163 and a second over-drape portion 1165. The first over-drape portion 1163 extends over the first side 1134 of the shaped dressing bolster 1132 and extends further to form a drape flange, or drape extension 1164, which has a first side 1166 and a second, inward-facing side (not explicitly shown). An aperture 1181 is formed on a portion of the first over-drape 1163. The aperture 1181 is for allowing fluid communication with a reduced-pressure interface (e.g., reduced-pressure interface 92 in FIG. 1)

The second, inward-facing side of the drape extension 1164 is placed on a first side 1167 of the second over-drape portion 1165 and coupled, such as by an adhesive, bond 1169, other coupling technique or device, such as those previously mentioned. The first drape portion 1163 may include the plurality of folds 1173, or bellows. The folds 1173 allow the first drape portion 1163 to expand if needed. For example, if the dressing assembly 1130 is used on a joint, when the joint is flexed, the drape portion 1163 is extended using the folds 1173. Additional drape material may be released from the folds 1173 to facilitate movement. The second, inward-facing side of the second drape portion 1165 may have an adhesive on a portion and may have a treatment area aperture (see by analogy treatment area aperture 1271 in FIG. 17). The folds 1173 may also be formed as ridges that in cross section would appear as accordion-like ridges that flatten out when stretched and thereby provide additional material.

One or more release members 1182 may be releasably coupled to the first side 1167 of the second drape portion 1165. Four release members 1182 are shown in the illustrative embodiment of FIG. 15. The release members 1182 provide stiffness and help during deployment of the dressing assembly 1130. The release members 1182 are typically either casting paper or a film held on the first side 1167 of the second drape portion 1165.

Figure 17:
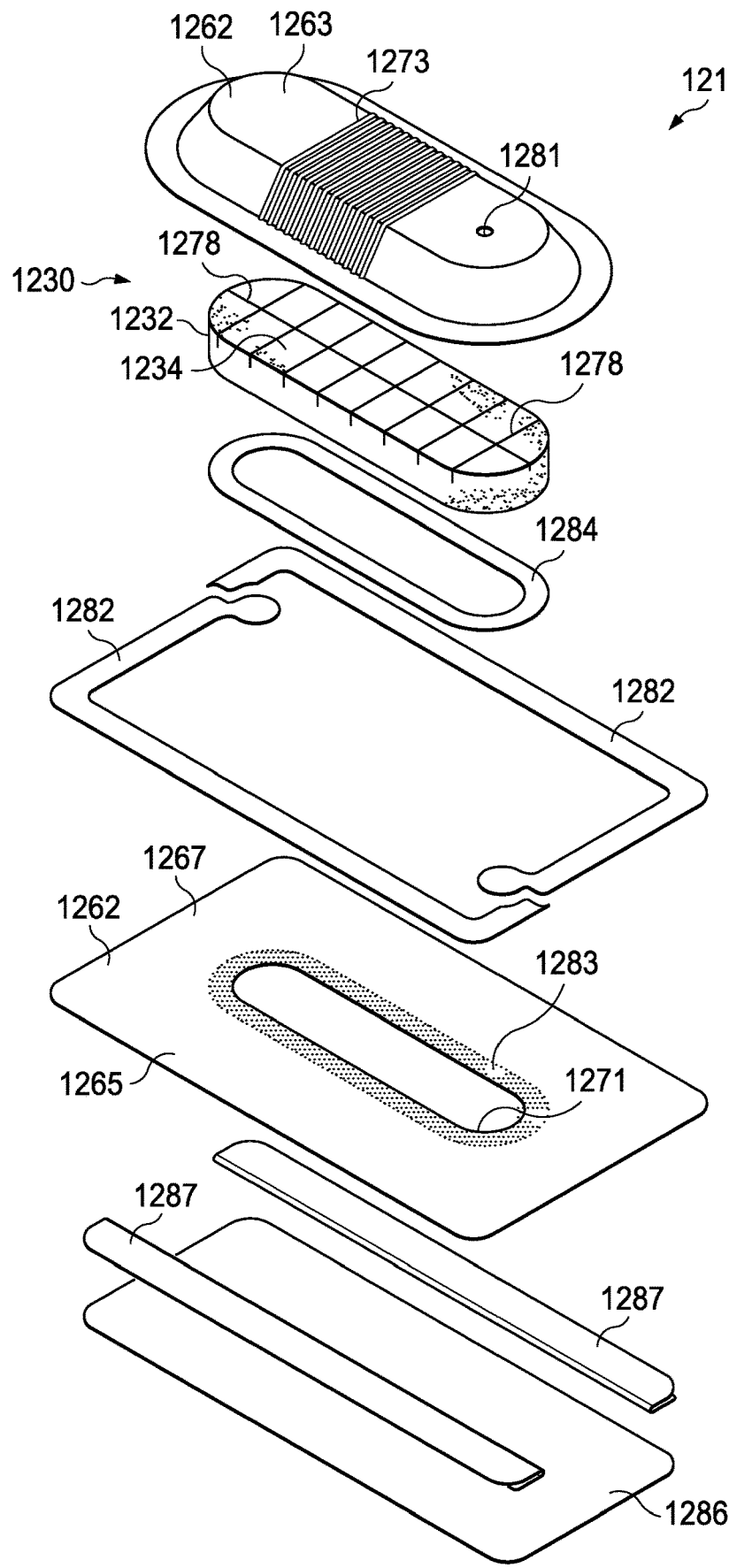
FIG. 17 is an exploded, schematic, perspective view of an illustrative embodiment of a dressing assembly.

Referring now primarily to FIG. 17, an exploded perspective view of a portion of a system 1210 for treating tissue, e.g., subcutaneous tissue, a linear wound, area wound, other wound, or graft is presented. The portion of the system 1210 presented in FIG. 17 is shown in a pre-deployment state and in an exploded view. The system 1210 is analogous in most respects to the system 1110 of FIGS. 15-16, and to indicate corresponding parts, the reference numerals have been indexed by 100 and may not be further mentioned. The system 1210 includes a dressing assembly 1230, which includes a shaped dressing bolster 1232. The shaped dressing bolster 1232 is the same as shaped dressing bolster 1132, but the flexibility notches 1278 are both lateral and longitudinal.

The first side 1234 of the shaped dressing bolster 1232 is covered by an over-drape 1262, which may include a first drape portion 1263 and a second drape portion 1265. The first drape portion 1263 includes folds 1273 and an aperture 1281. The second drape portion 1265 is formed with a treatment area aperture 1271 that provides an opening for at least a portion of the shaped dressing bolster 1232 (or a comfort layer) to be directly against a patient's epidermis or treatment site. The second drape portion 1265 has first side 1267 and has an adhesive 1283 applied on a portion of the first side 1267. The adhesive 1283 is used primarily during manufacture to hold the shaped dressing bolster 1232 against the second drape portion 1265 during assembly and also used to help hold the shaped dressing bolster 1232 during use. Before applying the shaped dressing bolster 1232 against the adhesive 1283, the adhesive 1283 is covered by a center releaseable member 1284. Outboard of the adhesive 1283 on the first side 1267 are releaseable members 1282 that provides stiffness to the over-drape 1262 during deployment.

The second, inward-facing side (not explicitly shown but opposite side of the first side 1267) of the second drape portion 1265 may be covered with an adhesive. In the pre-deployment state, this adhesive is covered by a bottom release member 1286 and side release members 1287.

Once assembled, the portion of the system 1210 resembles the portion of the system 1120 of FIG. 15. The use and design may vary, but in one illustrative embodiment, the portion of the system 1210 may deployed as will be described. The bottom release liner 1286 is removed and the exposed adhesive on the second, inward-facing side of the second drape portion 1265 is placed against a portion of the patient's epidermis beginning at one end and may be placed over a linear wound. After smoothly applying the second drape portion 1265, the side release members 1287 are removed. The release members 1282 on the first side 1267 of the over-drape 1262 are removed. A reduced-pressure interface is coupled to the aperture 1282 in the first over-drape portion 1263. The center release member 1284 was already removed during manufacture.

With respect to manufacturing the systems and components described above, the components and their assembly have been presented. In applying and coupling an over-drape to the first surface of a shaped dressing bolster, it may be desirable to utilize a press to remove any wrinkles that may otherwise result or remain. The medical bolster material of the shaped dressing assembly may be cut using a die cut or by hand with a router.

According to another illustrative embodiment, a reduced-pressure system for treating a tissue site includes a directed-force member, which has a non-orthogonal edge, e.g., a curved edge, a slanted or angled edged, or an edge with a portion of a drape adhered to the edge, for evenly distributing a force when placed under reduced-pressure. The directed-force member may be formed as a foam member with a plurality of channels for transmitting a fluid. The reduced-pressure system further includes the drape for providing a fluid seal over at least a portion of the directed-force member and a patient's epidermis. The system also may have a reduced-pressure conduit for fluidly coupling a reduced-pressure source and the directed-force member. In one illustrative embodiment, the directed-force member is a foam member with a tapered edge. When reduced-pressure is delivered by the reduced-pressure source to an interior portion through the drape, the reduced pressure causes the directed-force member to exert a force. The force may include a vertical force against a patient's epidermis or other tissue that may penetrate to more than 1 millimeter, more than 2 millimeters, more than 3 millimeters, more than 4 millimeters, more than 5 millimeters, more than 7 millimeters, and even deeper. The vertical force may help approximate dead space and voids. The force may be or include a closing force.

According to another illustrative embodiment, a reduced-pressure, force-generating dressing assembly includes a directed-force member that has an oblique edge for evenly distributing a force when placed under reduced-pressure. The directed-force member has a top side and a bottom side. The directed-force member is formed from a medical bolster material, which has a plurality of channels. The flow channels may be interconnected, e.g., a foam. The dressing assembly may further include a drape for providing a fluid seal over at least a portion of the directed-force member and a patient's epidermis. The directed-force member may have an angled extremity. Alternatively, the directed-force member may have an arcuate extremity. The dressing assembly may also have a comfort layer coupled to the bottom side of the directed-force member. The comfort layer may be a breathable dry layer coupled to the bottom side of the directed-force member or any other material that helps to avoid maceration of the skin or skin irritation of any kind.

According to another illustrative embodiment, a method of treating a damaged subcutaneous tissue on a patient includes positioning a shaped dressing bolster over the damaged subcutaneous tissue. The shaped dressing bolster has an oblique extremity and is formed from a medical bolster material. The method further includes deploying an over-drape over the shaped dressing bolster and a portion of the patient's epidermis to provide a fluid seal and providing a reduced-pressure source. The method also includes coupling a reduced-pressure interface to the drape and fluidly coupling a reduced-pressure delivery conduit to the reduced-pressure source and to the reduced-pressure interface. The method also involves activating the reduced-pressure source to provide reduced pressure to the shaped dressing bolster to develop a compressive force and a closing force. The compressive force may be realized at a subcutaneous tissue or other subdermal anatomy.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

We claim:

1. A dressing assembly for treating a tissue site, comprising:
   a dressing bolster comprising a super-absorbent material;
   an inner layer having a treatment aperture;
   a breathable dry layer positioned between the dressing bolster and the inner layer; and
   an over-drape positioned over the dressing bolster and inner layer;
   wherein the dressing bolster has a characteristic of distributing a compressive force when placed under a reduced pressure.

2. The dressing assembly of claim 1, wherein the dressing bolster has an oblique extremity.

3. The dressing assembly of claim 2, wherein the extremity of the dressing bolster has a trapezoidal shape in cross-section.

4. The dressing assembly of claim 2, wherein the extremity of the dressing bolster has an arcuate shape in at least two orthogonal cross-sectionals.

5. The dressing assembly of claim 1, wherein the dressing bolster has a rectangular shape.

6. The dressing assembly of claim 1, wherein the dressing bolster further comprises a plurality of lateral notches.

7. The dressing assembly of claim 1, wherein the dressing bolster has a first surface and a second surface, and wherein the over-drape is coupled to at least a portion of the first surface of the dressing bolster.

8. The dressing assembly of claim 1, wherein the dressing bolster comprises an isotropic material.

9. The dressing assembly of claim 1, wherein the dressing bolster comprises an anisotropic material.

10. The dressing assembly of claim 1, wherein the super-absorbent material of the dressing bolster is operable under reduced pressure to develop the compressive force that increases with the addition of fluid to the super-absorbent material.

11. The dressing assembly of claim 1, wherein the breathable dry layer comprises a hydrophilic non-woven material.

12. The dressing assembly of claim 1, wherein a portion of the over-drape is coupled to the inner layer.

13. The dressing assembly of claim 1, wherein the inner layer comprises a silicone material.

14. The dressing assembly of claim 1, wherein:
   the breathable dry layer has a first surface and a second surface;
   the super-absorbent material of the dressing bolster has a first surface and a second surface and is operable to increase in rigidity with the addition of a fluid; and
   the second surface of the super-absorbent material is coupled, at least in part, to the first surface of the breathable dry layer.

15. The dressing assembly of claim 1, wherein:
   the over-drape extends over the dressing bolster and extends beyond the dressing bolster to form a drape extension; and
   the inner layer is coupled to at least a portion of the drape extension on an inward-facing surface.

16. A reduced-pressure system for treating a tissue site, comprising:
- a reduced-pressure interface coupled to the over-drape of the dressing assembly of claim 1;
- a reduced-pressure delivery conduit for fluidly coupling to the reduced-pressure interface; and
- a reduced-pressure source.

17. A method of treating a tissue site, comprising:
- positioning a dressing assembly over the tissue site, wherein the dressing assembly comprises:
  - a super-absorbent bolster layer,
  - an inner layer having a treatment aperture, and
  - a breathable dry layer positioned between the super-absorbent bolster layer and the inner layer;
- deploying an over-drape over the dressing assembly and a portion of an epidermis to provide a fluid seal;
- coupling a reduced-pressure interface to the over-drape;
- fluidly coupling a conduit to a reduced-pressure source and to the reduced-pressure interface;
- activating the reduced-pressure source to provide reduced pressure to the dressing assembly.

18. The method of claim 17, wherein the step of positioning the dressing assembly over the tissue site includes the step of deploying the dressing assembly at least partially over intact epidermis.

19. The method of claim 17, wherein the breathable dry layer comprises a hydrophilic non-woven material.

20. The method of claim 17, wherein the inner layer comprises a silicone material.

* * * * *